US009376724B2

(12) United States Patent
Rudi et al.

(10) Patent No.: US 9,376,724 B2
(45) Date of Patent: Jun. 28, 2016

(54) METHOD FOR IDENTIFYING NEONATES AT RISK FOR NECROTIZING ENTEROCOLITIS

(75) Inventors: Knut Rudi, Vestby (NO); Heidi Cecilie Vebø, Ås (NO); Monika Sekelja, Oslo (NO); Morten Isaksen, Oslo (NO)

(73) Assignee: GENETIC ANALYSIS AS (NO)

( * ) Notice: Subject to any disclaimer, the term of this patent is extended or adjusted under 35 U.S.C. 154(b) by 73 days.

(21) Appl. No.: 13/984,079

(22) PCT Filed: Feb. 16, 2012

(86) PCT No.: PCT/GB2012/050353
§ 371 (c)(1),
(2), (4) Date: Oct. 15, 2013

(87) PCT Pub. No.: WO2012/110822
PCT Pub. Date: Aug. 23, 2012

(65) Prior Publication Data
US 2014/0031255 A1 Jan. 30, 2014

(30) Foreign Application Priority Data
Feb. 16, 2011 (GB) .................................. 1102693.7

(51) Int. Cl.
*C12Q 1/68* (2006.01)
*C12P 19/34* (2006.01)
*C07H 21/04* (2006.01)

(52) U.S. Cl.
CPC .......... *C12Q 1/689* (2013.01); *C12Q 2600/118* (2013.01)

(58) Field of Classification Search
USPC .............................. 435/6.12, 91.2; 536/24.33
See application file for complete search history.

(56) References Cited

U.S. PATENT DOCUMENTS

| 4,267,234 | A | 5/1981 | Rembaum |
| 4,267,235 | A | 5/1981 | Rembaum et al. |
| 4,552,812 | A | 11/1985 | Margel et al. |
| 4,677,138 | A | 6/1987 | Margel |
| 4,717,655 | A | 1/1988 | Fulwyler |
| 4,774,189 | A | 9/1988 | Schwartz |
| 5,073,498 | A | 12/1991 | Schwartz et al. |
| 5,194,300 | A | 3/1993 | Cheung |
| 5,326,692 | A | 7/1994 | Brinkley et al. |
| 5,573,909 | A | 11/1996 | Singer et al. |
| 5,700,637 | A * | 12/1997 | Southern ...................... 435/6.12 |
| 5,716,855 | A | 2/1998 | Lerner et al. |
| 5,723,218 | A | 3/1998 | Haugland et al. |
| 5,786,219 | A | 7/1998 | Zhang et al. |
| 2007/0254837 | A1* | 11/2007 | Hardin et al. ................... 514/12 |
| 2011/0104692 | A1 | 5/2011 | Rudi et al. |

FOREIGN PATENT DOCUMENTS

| WO | 9714028 A2 | 4/1997 |
| WO | 9851693 A1 | 11/1998 |
| WO | 9919515 A1 | 4/1999 |
| WO | 9950448 A2 | 10/1999 |
| WO | 0039587 A1 | 7/2000 |
| WO | 0113119 A1 | 2/2001 |
| WO | 0113120 A1 | 2/2001 |
| WO | 0118524 A2 | 3/2001 |
| WO | 0153525 A2 | 7/2001 |
| WO | 0159432 A2 | 8/2001 |
| WO | 0200336 A2 | 1/2002 |
| WO | 2009033011 A1 | 3/2009 |
| WO | 2009123736 A2 | 10/2009 |

OTHER PUBLICATIONS

International Preliminary Report on Patentability; International Application No. PCT/GB2012/050353; International Filing Date Feb. 16, 2012; Date of Mailing Aug. 29, 2013; 9 pages.
Bjorkstrom et al.; Intestinal Flora in Very Low-Birth Weight Infants; Acta Paediatrica; 98(11) pp. 1762-1767; (2009).
de la Cochetiere et al.; "Early Intestinal Bacterial Colonization and Necrotizing Enterocolitis in Premature Infants: The Putative Role of Clostridium"; Pediatric Research; 56(3); pp. 366-370; (2004).
Hoy et al.; "Duodenal Microflora in Very-Low-Birth-Weight Neonates and Relation to Necrotizing Enterocolitis"; Journal of Clinical Microbiology; 38(12); pp. 4539-4547; (2000).
Millar et al.; "Application of 16S rRNA Gene PCR to Study Bowel Flora of Preterm Infants With and Without Necrotizing Enterocolitis"; Journal of Clinical Microbiology; 34(10); pp. 2506-2510; (1996).
Morowitz et al.; "Redefiing the Role of Intestinal Microbes in the Pathogenesis of Necrotizing Enterocolitis"; Pediatrics; 125; pp. 777-785; (2010).
Mshvildadze, et al.; "Intestinal Microbial Ecology in Premature Infants Assessed with Non-Culture-Based Techniques"; The Journal of Pediatrics; 156(1); pp. 20-25; (2010).
Nadkarni et al.; "Determination of Bacterial Load by Real-Time PCR Using a Broad-Range (Universal) Probe and Primers Set"; Microbiology; 148; pp. 257-266; (2002).
Palmer et al.; "Development of the Human Infant Intestinal Microbiota"; PLoS Biology; 5(7); pp. 1556-1563; (2007).

(Continued)

*Primary Examiner* — Kenneth R. Horlick
*Assistant Examiner* — Joyce Tung
(74) *Attorney, Agent, or Firm* — Cantor Colburn LLP

(57) ABSTRACT

The invention provides a method for identifying a neonatal subject at risk for NEC, said method comprising (a) profiling the microbiota in a sample from the GI tract of said subject prior to a conclusive diagnosis of NEC and/or prior to full onset of NEC, (b1) comparing said profile to a standard microbiota profile obtained from corresponding samples from neonatal subjects with NEC or subjects which later developed NEC and determining the degree of correlation between said profile and the standard profile(s), and/or (b2) comparing said profile to a standard microbiota profile obtained from corresponding samples from neonatal subjects which did not develop NEC and determining the degree of correlation between said profile and the standard profile, and (c) identifying the subject as being at risk of NEC if significant correlation is observed in (b1) and/or significant correlation is not seen in (b2). An oligonucleotide probe set for use in the method of the invention, and kits containing the same, are also provided.

21 Claims, 2 Drawing Sheets

(56) References Cited

OTHER PUBLICATIONS

Figure 1:
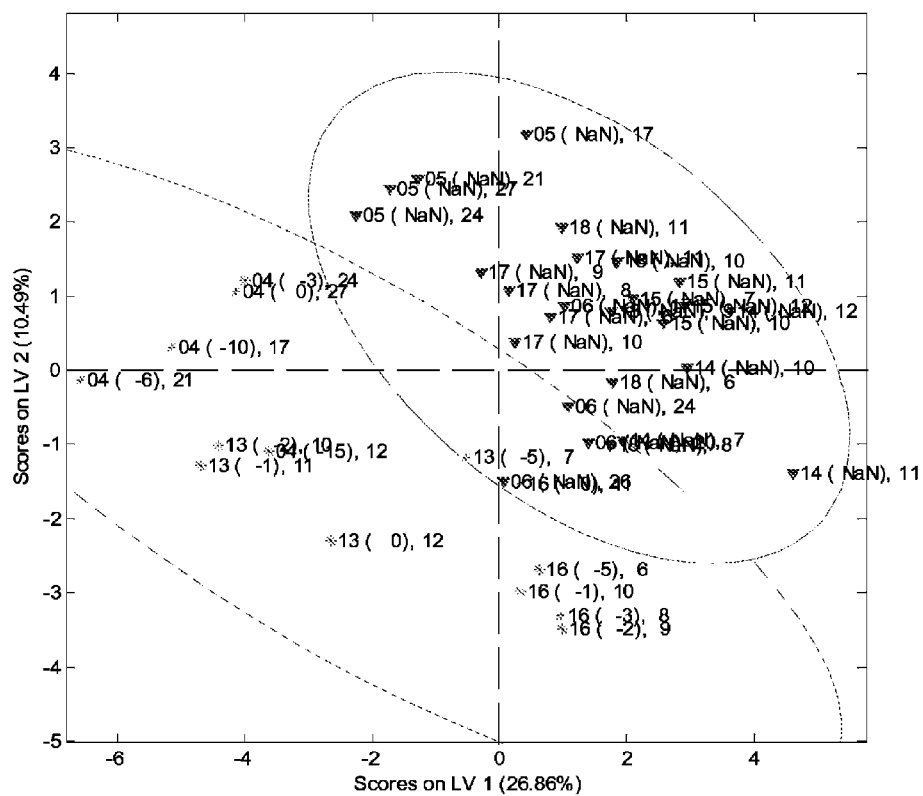

International Search Report and Written Opinion; International Application No. PCT/GB2012/050353; International Filing Date Feb. 16, 2012; Date of Mailing Apr. 2, 2012; 15 pages.

Rudi et al.; "Quantification of Toxic Cyanobacteria in Water by Use of Competitive PCR Followed by Sequence-Specific Labeling of Oligonucleotide Probes"; Applied Environmental Microbiology; 64(7); pp. 2639-2643; (1998).

Rudi et al.; "Alignment-Independent Comparisons of Human Gastrointestinal Tract Microbial Communities in a Multidimensional 16S rRNA Gene Evolutionary Space"; Applied and Environmental Microbiology; 73(8); pp. 2727-2734; (2007).

Syvanen et al.; "A Primer-Guided Nucleotide Incorporation Assay in the Genotyping of Apolipoprotein E"; Genomics; 8; pp. 684-692; (1990).

Wang et al.; "16S rRNA Gene-Based Analysis of Fecal Microbiota from Preterm Infants With and Without Necrotizing Enterocolitis"; The ISME Journal; 3; pp. 944-954; (2009).

Weisburg et al.; "16S Ribosomal DNA Amplification for Phylogenetic Study"; Journal of Bacteriology; 173(2); pp. 697-703; (1991).

Young et al.; "Biomarkers for Infants at Risk for Necrotizing Enterocolitis: Clues to Prevention?"; Pediatric Research; 65(5) Pt 2; pp. 91R-97R; (2009).

* cited by examiner

SEQUENCE LISTING

<160> NUMBER OF SEQ ID NOS: 82

<210> SEQ ID NO 1
<211> LENGTH: 22
<212> TYPE: DNA
<213> ORGANISM: Artificial Sequence
<220> FEATURE:
<223> OTHER INFORMATION: Probe

<400> SEQUENCE: 1
cacatgagcg tcagtacatt cc                                              22

<210> SEQ ID NO 2
<211> LENGTH: 28
<212> TYPE: DNA
<213> ORGANISM: Artificial Sequence
<220> FEATURE:
<223> OTHER INFORMATION: Probe

<400> SEQUENCE: 2
tgttgtggtt aataaccgca gcaattga                                        28

<210> SEQ ID NO 3
<211> LENGTH: 16
<212> TYPE: DNA
<213> ORGANISM: Artificial Sequence
<220> FEATURE:
<223> OTHER INFORMATION: Probe

<400> SEQUENCE: 3
ggacaacgct tgccac                                                     16

<210> SEQ ID NO 4
<211> LENGTH: 18
<212> TYPE: DNA
<213> ORGANISM: Artificial Sequence
<220> FEATURE:
<223> OTHER INFORMATION: Probe

<400> SEQUENCE: 4
accgctacac aggaaatt                                                   18

<210> SEQ ID NO 5
<211> LENGTH: 26
<212> TYPE: DNA
<213> ORGANISM: Artificial Sequence
<220> FEATURE:
<223> OTHER INFORMATION: Probe

<400> SEQUENCE: 5
ggaattccac tttcctctcc gatact                                          26

<210> SEQ ID NO 6
<211> LENGTH: 17
<212> TYPE: DNA
<213> ORGANISM: Artificial Sequence
<220> FEATURE:
<223> OTHER INFORMATION: Probe

<400> SEQUENCE: 6
gcacctgtct cacagtt                                                    17

<210> SEQ ID NO 7
<211> LENGTH: 17
<212> TYPE: DNA
<213> ORGANISM: Artificial Sequence

```
<220> FEATURE:
<223> OTHER INFORMATION: Probe

<400> SEQUENCE: 7
gtttccaatg accctcc                                                    17

<210> SEQ ID NO 8
<211> LENGTH: 14
<212> TYPE: DNA
<213> ORGANISM: Artificial Sequence
<220> FEATURE:
<223> OTHER INFORMATION: Probe

<400> SEQUENCE: 8
cgtcagggga cgtt                                                       14

<210> SEQ ID NO 9
<211> LENGTH: 14
<212> TYPE: DNA
<213> ORGANISM: Artificial Sequence
<220> FEATURE:
<223> OTHER INFORMATION: Probe

<400> SEQUENCE: 9
ccccgctgaa agtg                                                       14

<210> SEQ ID NO 10
<211> LENGTH: 18
<212> TYPE: DNA
<213> ORGANISM: Artificial Sequence
<220> FEATURE:
<223> OTHER INFORMATION: Probe

<400> SEQUENCE: 10
cactcctcaa gggaacaa                                                   18

<210> SEQ ID NO 11
<211> LENGTH: 18
<212> TYPE: DNA
<213> ORGANISM: Artificial Sequence
<220> FEATURE:
<223> OTHER INFORMATION: Probe

<400> SEQUENCE: 11
agcgtattaa gctcacca                                                   18

<210> SEQ ID NO 12
<211> LENGTH: 13
<212> TYPE: DNA
<213> ORGANISM: Artificial Sequence
<220> FEATURE:
<223> OTHER INFORMATION: Probe

<400> SEQUENCE: 12
acgcttgcac cct                                                        13

<210> SEQ ID NO 13
<211> LENGTH: 22
<212> TYPE: DNA
<213> ORGANISM: Artificial Sequence
<220> FEATURE:
<223> OTHER INFORMATION: Probe

<400> SEQUENCE: 13
cgatccgaaa accttcttca ct                                              22
```

```
<210> SEQ ID NO 14
<211> LENGTH: 16
<212> TYPE: DNA
<213> ORGANISM: Artificial Sequence
<220> FEATURE:
<223> OTHER INFORMATION: Probe

<400> SEQUENCE: 14
cactctcaca cccgtt                                                        16

<210> SEQ ID NO 15
<211> LENGTH: 15
<212> TYPE: DNA
<213> ORGANISM: Artificial Sequence
<220> FEATURE:
<223> OTHER INFORMATION: Probe

<400> SEQUENCE: 15
ccgtcaaggg acaag                                                         15

<210> SEQ ID NO 16
<211> LENGTH: 17
<212> TYPE: DNA
<213> ORGANISM: Artificial Sequence
<220> FEATURE:
<223> OTHER INFORMATION: Probe

<400> SEQUENCE: 16
gttgctcggt cagactt                                                       17

<210> SEQ ID NO 17
<211> LENGTH: 20
<212> TYPE: DNA
<213> ORGANISM: Artificial Sequence
<220> FEATURE:
<223> OTHER INFORMATION: Probe

<400> SEQUENCE: 17
cgtggctttc tgattaggta                                                    20

<210> SEQ ID NO 18
<211> LENGTH: 21
<212> TYPE: DNA
<213> ORGANISM: Artificial Sequence
<220> FEATURE:
<223> OTHER INFORMATION: Probe

<400> SEQUENCE: 18
tgcttattca acgggtaaac t                                                  21

<210> SEQ ID NO 19
<211> LENGTH: 19
<212> TYPE: DNA
<213> ORGANISM: Artificial Sequence
<220> FEATURE:
<223> OTHER INFORMATION: Probe

<400> SEQUENCE: 19
cgtaggcggt tcgtcgcgt                                                     19

<210> SEQ ID NO 20
<211> LENGTH: 24
<212> TYPE: DNA
<213> ORGANISM: Artificial Sequence
<220> FEATURE:
<223> OTHER INFORMATION: Probe
```

```
<400> SEQUENCE: 20
cggtgcttat tcgaaaggta cact                                          24

<210> SEQ ID NO 21
<211> LENGTH: 20
<212> TYPE: DNA
<213> ORGANISM: Artificial Sequence
<220> FEATURE:
<223> OTHER INFORMATION: Probe

<400> SEQUENCE: 21
agagctttac gaaccgaaat                                               20

<210> SEQ ID NO 22
<211> LENGTH: 19
<212> TYPE: DNA
<213> ORGANISM: Artificial Sequence
<220> FEATURE:
<223> OTHER INFORMATION: Probe

<400> SEQUENCE: 22
cggcagtctc tcatgagtt                                                19

<210> SEQ ID NO 23
<211> LENGTH: 17
<212> TYPE: DNA
<213> ORGANISM: Artificial Sequence
<220> FEATURE:
<223> OTHER INFORMATION: Probe

<400> SEQUENCE: 23
ccgctacaca tggagtt                                                  17

<210> SEQ ID NO 24
<211> LENGTH: 24
<212> TYPE: DNA
<213> ORGANISM: Artificial Sequence
<220> FEATURE:
<223> OTHER INFORMATION: Probe

<400> SEQUENCE: 24
cactaggaat tccgctctcc tctc                                          24

<210> SEQ ID NO 25
<211> LENGTH: 27
<212> TYPE: DNA
<213> ORGANISM: Artificial Sequence
<220> FEATURE:
<223> OTHER INFORMATION: Probe

<400> SEQUENCE: 25
caatcggagt tcttcgtgat atctaag                                       27

<210> SEQ ID NO 26
<211> LENGTH: 15
<212> TYPE: DNA
<213> ORGANISM: Artificial Sequence
<220> FEATURE:
<223> OTHER INFORMATION: Probe

<400> SEQUENCE: 26
gcaccacctg tcact                                                    15

<210> SEQ ID NO 27
```

```
<210> SEQ ID NO 27
<211> LENGTH: 22
<212> TYPE: DNA
<213> ORGANISM: Artificial Sequence
<220> FEATURE:
<223> OTHER INFORMATION: Probe

<400> SEQUENCE: 27
gttaaacagt ttcccaagcg ta                                            22

<210> SEQ ID NO 28
<211> LENGTH: 17
<212> TYPE: DNA
<213> ORGANISM: Artificial Sequence
<220> FEATURE:
<223> OTHER INFORMATION: Probe

<400> SEQUENCE: 28
cacctgtcac ttctgct                                                  17

<210> SEQ ID NO 29
<211> LENGTH: 17
<212> TYPE: DNA
<213> ORGANISM: Artificial Sequence
<220> FEATURE:
<223> OTHER INFORMATION: Probe

<400> SEQUENCE: 29
aggcggagtg tttattg                                                  17

<210> SEQ ID NO 30
<211> LENGTH: 17
<212> TYPE: DNA
<213> ORGANISM: Artificial Sequence
<220> FEATURE:
<223> OTHER INFORMATION: Probe

<400> SEQUENCE: 30
gcttcctcct ctggtac                                                  17

<210> SEQ ID NO 31
<211> LENGTH: 22
<212> TYPE: DNA
<213> ORGANISM: Artificial Sequence
<220> FEATURE:
<223> OTHER INFORMATION: Probe

<400> SEQUENCE: 31
cgatacgaat accttcttcg tt                                            22

<210> SEQ ID NO 32
<211> LENGTH: 24
<212> TYPE: DNA
<213> ORGANISM: Artificial Sequence
<220> FEATURE:
<223> OTHER INFORMATION: Probe

<400> SEQUENCE: 32
tcaacctggg aactgcatct gata                                          24

<210> SEQ ID NO 33
<211> LENGTH: 13
<212> TYPE: DNA
<213> ORGANISM: Artificial Sequence
<220> FEATURE:
<223> OTHER INFORMATION: Probe

<400> SEQUENCE: 33
```
tctcgcgagg ttg                                                          13

<210> SEQ ID NO 34
<211> LENGTH: 17
<212> TYPE: DNA
<213> ORGANISM: Artificial Sequence
<220> FEATURE:
<223> OTHER INFORMATION: Probe

<400> SEQUENCE: 34 ccccoctcta caagact                                                      17

<210> SEQ ID NO 35
<211> LENGTH: 16
<212> TYPE: DNA
<213> ORGANISM: Artificial Sequence
<220> FEATURE:
<223> OTHER INFORMATION: Probe

<400> SEQUENCE: 35
cgactcgttg taccag                                                       16

<210> SEQ ID NO 36
<211> LENGTH: 22
<212> TYPE: DNA
<213> ORGANISM: Artificial Sequence
<220> FEATURE:
<223> OTHER INFORMATION: Probe

<400> SEQUENCE: 36
ggaatgtact gacgctcatg tg                                                22

<210> SEQ ID NO 37
<211> LENGTH: 28
<212> TYPE: DNA
<213> ORGANISM: Artificial Sequence
<220> FEATURE:
<223> OTHER INFORMATION: Probe

<400> SEQUENCE: 37
tcaattgctg cggttattaa ccacaaca                                          28

<210> SEQ ID NO 38
<211> LENGTH: 16
<212> TYPE: DNA
<213> ORGANISM: Artificial Sequence
<220> FEATURE:
<223> OTHER INFORMATION: Probe

<400> SEQUENCE: 38
gtggcaagcg ttgtcc                                                       16

<210> SEQ ID NO 39
<211> LENGTH: 18
<212> TYPE: DNA
<213> ORGANISM: Artificial Sequence
<220> FEATURE:
<223> OTHER INFORMATION: Probe

<400> SEQUENCE: 39
aatttcctgt gtagcggt                                                     18

<210> SEQ ID NO 40
<211> LENGTH: 26
<212> TYPE: DNA

<213> ORGANISM: Artificial Sequence
<220> FEATURE:
<223> OTHER INFORMATION: Probe

<400> SEQUENCE: 40
agtatcggag aggaaagtgg aattcc                                      26

<210> SEQ ID NO 41
<211> LENGTH: 17
<212> TYPE: DNA
<213> ORGANISM: Artificial Sequence
<220> FEATURE:
<223> OTHER INFORMATION: Probe

<400> SEQUENCE: 41
aactgtgaga caggtgc                                                17

<210> SEQ ID NO 42
<211> LENGTH: 17
<212> TYPE: DNA
<213> ORGANISM: Artificial Sequence
<220> FEATURE:
<223> OTHER INFORMATION: Probe

<400> SEQUENCE: 42
ggagggtcat tggaaac                                                17

<210> SEQ ID NO 43
<211> LENGTH: 14
<212> TYPE: DNA
<213> ORGANISM: Artificial Sequence
<220> FEATURE:
<223> OTHER INFORMATION: Probe

<400> SEQUENCE: 43
aacgtcccct gacg                                                   14

<210> SEQ ID NO 44
<211> LENGTH: 14
<212> TYPE: DNA
<213> ORGANISM: Artificial Sequence
<220> FEATURE:
<223> OTHER INFORMATION: Probe

<400> SEQUENCE: 44
cactttcagc gggg                                                   14

<210> SEQ ID NO 45
<211> LENGTH: 18
<212> TYPE: DNA
<213> ORGANISM: Artificial Sequence
<220> FEATURE:
<223> OTHER INFORMATION: Probe

<400> SEQUENCE: 45
ttgttccctt gaggagtg                                               18

<210> SEQ ID NO 46
<211> LENGTH: 18
<212> TYPE: DNA
<213> ORGANISM: Artificial Sequence
<220> FEATURE:
<223> OTHER INFORMATION: Probe

<400> SEQUENCE: 46
tggtgagctt aatacgct                                               18

<210> SEQ ID NO 47
<211> LENGTH: 13
<212> TYPE: DNA
<213> ORGANISM: Artificial Sequence
<220> FEATURE:
<223> OTHER INFORMATION: Probe

<400> SEQUENCE: 47
agggtgcaag cgt                                                          13

<210> SEQ ID NO 48
<211> LENGTH: 22
<212> TYPE: DNA
<213> ORGANISM: Artificial Sequence
<220> FEATURE:
<223> OTHER INFORMATION: Probe

<400> SEQUENCE: 48
agtgaagaag gttttcggat cg                                                22

<210> SEQ ID NO 49
<211> LENGTH: 16
<212> TYPE: DNA
<213> ORGANISM: Artificial Sequence
<220> FEATURE:
<223> OTHER INFORMATION: Probe

<400> SEQUENCE: 49
aacgggtgtg agagtg                                                       16

<210> SEQ ID NO 50
<211> LENGTH: 15
<212> TYPE: DNA
<213> ORGANISM: Artificial Sequence
<220> FEATURE:
<223> OTHER INFORMATION: Probe

<400> SEQUENCE: 50
cttgtccctt gacgg                                                        15

<210> SEQ ID NO 51
<211> LENGTH: 17
<212> TYPE: DNA
<213> ORGANISM: Artificial Sequence
<220> FEATURE:
<223> OTHER INFORMATION: Probe

<400> SEQUENCE: 51
aagtctgacc gagcaac                                                      17

<210> SEQ ID NO 52
<211> LENGTH: 20
<212> TYPE: DNA
<213> ORGANISM: Artificial Sequence
<220> FEATURE:
<223> OTHER INFORMATION: Probe

<400> SEQUENCE: 52
tacctaatca gaaagccacg                                                   20

<210> SEQ ID NO 53
<211> LENGTH: 21
<212> TYPE: DNA
<213> ORGANISM: Artificial Sequence
<220> FEATURE:

<223> OTHER INFORMATION: Probe

<400> SEQUENCE: 53
agtttacccg ttgaataagc a                                     21

<210> SEQ ID NO 54
<211> LENGTH: 19
<212> TYPE: DNA
<213> ORGANISM: Artificial Sequence
<220> FEATURE:
<223> OTHER INFORMATION: Probe

<400> SEQUENCE: 54
acgcgacgaa ccgcctacg                                        19

<210> SEQ ID NO 55
<211> LENGTH: 24
<212> TYPE: DNA
<213> ORGANISM: Artificial Sequence
<220> FEATURE:
<223> OTHER INFORMATION: Probe

<400> SEQUENCE: 55
agtgtacctt tcgaataagc accg                                  24

<210> SEQ ID NO 56
<211> LENGTH: 20
<212> TYPE: DNA
<213> ORGANISM: Artificial Sequence
<220> FEATURE:
<223> OTHER INFORMATION: Probe

<400> SEQUENCE: 56
atttcggttc gtaaagctct                                       20

<210> SEQ ID NO 57
<211> LENGTH: 19
<212> TYPE: DNA
<213> ORGANISM: Artificial Sequence
<220> FEATURE:
<223> OTHER INFORMATION: Probe

<400> SEQUENCE: 57
aactcatgag agactgccg                                        19

<210> SEQ ID NO 58
<211> LENGTH: 17
<212> TYPE: DNA
<213> ORGANISM: Artificial Sequence
<220> FEATURE:
<223> OTHER INFORMATION: Probe

<400> SEQUENCE: 58
aactccatgt gtagcgg                                          17

<210> SEQ ID NO 59
<211> LENGTH: 24
<212> TYPE: DNA
<213> ORGANISM: Artificial Sequence
<220> FEATURE:
<223> OTHER INFORMATION: Probe

<400> SEQUENCE: 59
gagaggagag cggaattcct agtg                                  24

<210> SEQ ID NO 60
<211> LENGTH: 27
<212> TYPE: DNA
<213> ORGANISM: Artificial Sequence
<220> FEATURE:
<223> OTHER INFORMATION: Probe

<400> SEQUENCE: 60
cttagatatc acgaagaact ccgattg                               27

<210> SEQ ID NO 61
<211> LENGTH: 15
<212> TYPE: DNA
<213> ORGANISM: Artificial Sequence
<220> FEATURE:
<223> OTHER INFORMATION: Probe

<400> SEQUENCE: 61
agtgacaggt ggtgc                                            15

<210> SEQ ID NO 62
<211> LENGTH: 22
<212> TYPE: DNA
<213> ORGANISM: Artificial Sequence
<220> FEATURE:
<223> OTHER INFORMATION: Probe

<400> SEQUENCE: 62
tacgcttggg aaactgttta ac                                    22

<210> SEQ ID NO 63
<211> LENGTH: 17
<212> TYPE: DNA
<213> ORGANISM: Artificial Sequence
<220> FEATURE:
<223> OTHER INFORMATION: Probe

<400> SEQUENCE: 63
agcagaagtg acaggtg                                          17

<210> SEQ ID NO 64
<211> LENGTH: 17
<212> TYPE: DNA
<213> ORGANISM: Artificial Sequence
<220> FEATURE:
<223> OTHER INFORMATION: Probe

<400> SEQUENCE: 64
caataaacac tccgcct                                          17

<210> SEQ ID NO 65
<211> LENGTH: 17
<212> TYPE: DNA
<213> ORGANISM: Artificial Sequence
<220> FEATURE:
<223> OTHER INFORMATION: Probe

<400> SEQUENCE: 65
gtaccagagg aggaagc                                          17

<210> SEQ ID NO 66
<211> LENGTH: 22
<212> TYPE: DNA
<213> ORGANISM: Artificial Sequence
<220> FEATURE:
<223> OTHER INFORMATION: Probe

```
<400> SEQUENCE: 66
aacgaagaag gtattcgtat cg                                              22

<210> SEQ ID NO 67
<211> LENGTH: 24
<212> TYPE: DNA
<213> ORGANISM: Artificial Sequence
<220> FEATURE:
<223> OTHER INFORMATION: Probe

<400> SEQUENCE: 67
tatcagatgc agttcccagg ttga                                            24

<210> SEQ ID NO 68
<211> LENGTH: 13
<212> TYPE: DNA
<213> ORGANISM: Artificial Sequence
<220> FEATURE:
<223> OTHER INFORMATION: Probe

<400> SEQUENCE: 68
caacctcgcg aga                                                        13

<210> SEQ ID NO 69
<211> LENGTH: 17
<212> TYPE: DNA
<213> ORGANISM: Artificial Sequence
<220> FEATURE:
<223> OTHER INFORMATION: Probe

<400> SEQUENCE: 69
agtcttgtag agggggg                                                    17

<210> SEQ ID NO 70
<211> LENGTH: 16
<212> TYPE: DNA
<213> ORGANISM: Artificial Sequence
<220> FEATURE:
<223> OTHER INFORMATION: Probe

<400> SEQUENCE: 70
ctggtacaac gagtcg                                                     16

<210> SEQ ID NO 71
<211> LENGTH: 18
<212> TYPE: DNA
<213> ORGANISM: Artificial Sequence
<220> FEATURE:
<223> OTHER INFORMATION: Probe

<400> SEQUENCE: 71
tcctacggga ggcagcag                                                   18

<210> SEQ ID NO 72
<211> LENGTH: 20
<212> TYPE: DNA
<213> ORGANISM: Artificial Sequence
<220> FEATURE:
<223> OTHER INFORMATION: Probe

<400> SEQUENCE: 72
cggttacctt gttacgactt                                                 20

<210> SEQ ID NO 73
<211> LENGTH: 22
```

<212> TYPE: DNA
<213> ORGANISM: Artificial Sequence
<220> FEATURE:
<223> OTHER INFORMATION: Probe

<400> SEQUENCE: 73
cgtattaccg cggctgctgg ca                                              22

<210> SEQ ID NO 74
<211> LENGTH: 19
<212> TYPE: DNA
<213> ORGANISM: Artificial Sequence
<220> FEATURE:
<223> OTHER INFORMATION: Probe

<400> SEQUENCE: 74
gtattaccgc ggctgctgg                                                  19

<210> SEQ ID NO 75
<211> LENGTH: 20
<212> TYPE: DNA
<213> ORGANISM: Artificial Sequence
<220> FEATURE:
<223> OTHER INFORMATION: Probe

<400> SEQUENCE: 75
gtagcattcg attcgggcaa                                                 20

<210> SEQ ID NO 76
<211> LENGTH: 20
<212> TYPE: DNA
<213> ORGANISM: Artificial Sequence
<220> FEATURE:
<223> OTHER INFORMATION: Probe

<400> SEQUENCE: 76
aggaaggaag gaaggaaggg                                                 20

<210> SEQ ID NO 77
<211> LENGTH: 18
<212> TYPE: DNA
<213> ORGANISM: Artificial Sequence
<220> FEATURE:
<223> OTHER INFORMATION: Probe

<400> SEQUENCE: 77
tcctagtgac gccgtcga                                                   18

<210> SEQ ID NO 78
<211> LENGTH: 20
<212> TYPE: DNA
<213> ORGANISM: Artificial Sequence
<220> FEATURE:
<223> OTHER INFORMATION: Probe

<400> SEQUENCE: 78
cccttccttc cttccttcct                                                 20

<210> SEQ ID NO 79
<211> LENGTH: 18
<212> TYPE: DNA
<213> ORGANISM: Artificial Sequence
<220> FEATURE:
<223> OTHER INFORMATION: Probe

<400> SEQUENCE: 79

```
tcgacggcgt cactagga                                           18

<210> SEQ ID NO 80
<211> LENGTH: 22
<212> TYPE: DNA
<213> ORGANISM: Artificial Sequence
<220> FEATURE:
<223> OTHER INFORMATION: Probe

<400> SEQUENCE: 80
tgccagcagc cgcggtaata cg                                      22

<210> SEQ ID NO 81
<211> LENGTH: 19
<212> TYPE: DNA
<213> ORGANISM: Artificial Sequence
<220> FEATURE:
<223> OTHER INFORMATION: Probe

<400> SEQUENCE: 81
ccagcagccg cggtaatac                                          19

<210> SEQ ID NO 82
<211> LENGTH: 20
<212> TYPE: DNA
<213> ORGANISM: Artificial Sequence
<220> FEATURE:
<223> OTHER INFORMATION: Probe

<400> SEQUENCE: 82
ttgcccgaat cgaatgctac                                         20
```

METHOD FOR IDENTIFYING NEONATES AT RISK FOR NECROTIZING ENTEROCOLITIS

CROSS-REFERENCE TO RELATED APPLICATIONS

This application is a 371 of PCT/GB2012/050353 filed Feb. 16, 2013, which claims the benefit of priority to GB application No. 1102693.7, filed on Feb. 16, 2011, under provisions of 35 U.S.C. 119 and the International Convention for the protection of Industrial Property, which are incorporated herein by reference.

The present invention relates to a method for identifying neonatal subjects at risk for necrotizing enterocolitis (NEC). The method comprises profiling the microbiota of the gastrointestinal (GI) tract of a neonatal subject before onset of the condition and preferably as soon after birth as it is possible to detect microorganisms in a GI tract sample from the subject. That profile is then correlated either with standard profiles from neonatal subjects with NEC or which developed NEC and/or with standard profiles from neonatal subjects which did not develop NEC. The subject is at risk for NEC if its GI microbiota profile correlates with standard profiles from neonatal subjects with NEC or those which developed NEC, or if its GI microbiota profile does not correlate with standard profiles from neonatal subjects which did not develop NEC. The invention is based on the surprising observation that even at the earliest point at which microorganisms are detectable in the GI tract of neonatal subjects, the profile of GI microbiota in a subject that is at risk of developing NEC is sufficiently robust that it can be correlated with the standard samples described above and an accurate prediction of risk of NEC can be made. The invention also provides groups of bacteria that can form the basis of particularly robust profiles and suitable probes to analyse these groups of bacteria.

NEC is a GI emergency that commonly affects premature neonatal subjects (10% of neonates weighing less than 1500 g), although full term neonatal subjects can also be affected. In the premature subject weighing less than 1500 g mortality rates can be as high a 50% depending on the severity of the disease. In neonates weighing more than 2500 g mortality rates are between 0 and 20% depending on the severity of the disease and in neonates weighing less than 1000 g mortality rates are between 40 and 100%. For full term neonates mortality is on average around 5%.

NEC primarily effects the GI tact, where portions of the bowel undergo necrosis, but severe cases can cause profound impairment of multiple organ systems. The symptoms of the disease include feeding intolerance, delayed gastric emptying, abdominal distension, abdominal tenderness, or both, ileus/decreased bowel sounds, abdominal wall erythema, hematochezia, apnea, lethargy, decreased peripheral perfusion, shock (in advanced stages), cardiovascular collapse, bleeding diathesis (consumption coagulopathy), hyponatremia, metabolic acidosis, thrombocytopenia, leukopenia or leukocytosis with left shift, neutropenia, prolonged prothrombin time (PT) and activated partial thromboplastin time (aPTT) and decreasing fibrinogen and rising fibrin split products (in cases of consumption coagulopathy).

To date diagnosis is reactionary as it relies on the detection of physical signs, with and without the use of imagining studies such as abdominal radiography and ultrasonography, although laboratory blood testing such as cell counts, hemocrit levels and electrolytes and gases can assist in the diagnosis. Typically any or all of the following signs may contribute to a diagnosis of NEC: increased abdominal girth, visible intestinal loops, obvious abdominal distension and decreased bowel sounds, change in stool pattern, hematochezia, a palpable abdominal mass, erythema of the abdominal wall, respiratory failure, decreased peripheral perfusion, and circulatory collapse.

To date there are no reliable methods to identify neonates at risk for NEC. NEC can have a rapid onset and can occur soon after birth. The average age of onset of NEC in premature infants seems to be related to postconceptional age, with babies born earlier developing necrotizing enterocolitis later. The average age of onset has been reported to be 20.2 days for babies born at less than 30 weeks' estimated gestational age (EGA), 13.8 days for babies born at 31-33 weeks' EGA, and 5.4 days for babies born after 34 weeks' gestation. A method that can accurately predict, soon after birth, a neonate's risk of developing NEC would provide clinicians with a valuable tool as it would allow therapeutic intervention at an earlier stage or even prevention of NEC.

The eitology of NEC is still unresolved, but current thinking is that it has a multifactorial etiology, including intestinal ischemia, reperfusion injury with activation of proinflammatory cellular cascades and intestinal mucosal immaturity/dysfunction. It has been postulated that GI microbes have a role to play in the development of NEC. This latter hypothesis is however controversial as no study has yet conclusively identified a single microorganism, or profile of microorganisms, that correlates to the NEC disease state.

As a result of this controversy over the role of microorganisms in the etiology of NEC, diagnostic techniques based on detecting certain microbes or profiles of microbes in the GI tract of subjects suspected of having NEC have not been considered to be a viable approach to NEC diagnostics. This also means that a similar approach to the identification of subjects at risk of developing NEC has also been dismissed as fanciful, especial when a significant body of research points to the variability of the GI microbiota of neonatal subjects (both healthy and ill neonates).

The inventors have found that, on the contrary, as soon as microorganisms are detectable in the GI tract of a neonate, the microbiota profile seen at that time is very similar to the profiles seen later in life, whether or not NEC develops. In other words, contrary to current thinking, the microbiota in the GI tract of neonates is sufficiently stable to allow the skilled man to predict whether or not a neonate will develop NEC by correlating GI tract microbiota profiles obtained from that neonate as soon as microorganisms are detectable in its GI tract with standard microbiota profiles from neonatal subjects that have NEC or standard microbiota profiles from those which did not develop NEC, or even standard microbiota profiles from subjects that are known to have gone on to develop NEC.

Thus, in a first aspect the invention provides a method for identifying a neonatal subject at risk for NEC, said method comprising (a) profiling the microbiota in a sample from the GI tract of said subject prior to the onset of detectable symptoms of NEC, (b1) comparing said profile to a standard microbiota profile obtained from corresponding samples from neonatal subjects with NEC or subjects which later developed NEC and determining the degree of correlation between said profile and the standard profile(s), and/or (b2) comparing said profile to a standard microbiota profile obtained from corresponding samples from neonatal subjects which did not develop NEC and determining the degree of correlation between said profile and the standard profile, and (c) identifying the subject as being at risk of NEC if significant correlation is observed in (b1) and/or significant correlation is not seen in (b2).

In certain embodiments the subject is identified as being at risk of NEC if a more significant correlation is observed in (b1) than the correlation seen in (b2). Preferably the subject has not previously been confirmed as being at risk for NEC.

In this aspect the GI tract sample is collected from the subject and profiled prior to the onset of detectable symptoms of NEC. These symptoms include any or all of increased abdominal girth, visible intestinal loops, obvious abdominal distension and decreased bowel sounds, change in stool pattern, hematochezia, a palpable abdominal mass, erythema of the abdominal wall, respiratory failure, decreased peripheral perfusion, and circulatory collapse. Preferably the GI tract sample is collected from the subject and profiled prior to the onset of all or at least 9, 8, 7, 6, 5, 4, 3 or 2 of the above mentioned symptoms of NEC. In other embodiments the GI tract sample is collected from the subject and profiled prior to the full onset of NEC in the subject.

"Identifying a neonatal subject at risk for NEC" refers to the determination of the likelihood that the individual under investigation will develop NEC. This likelihood may be expressed as a numerical probability in some embodiments. The assessment of this likelihood may be by virtue of the extent a correlation is seen between the profile of the GI tract of said subject and the standard profile(s). Put differently, the method can be considered a method of predicting the risk a neonatal subject has of developing NEC. It is envisaged that the method of the invention will provide a robust indication of risk and so give a high degree of certainty to the skilled man in identifying subjects who will go on to develop NEC. The method can therefore also be considered to amount to a method for diagnosing NEC.

In other embodiments the subject may already be suspected of being at risk for NEC and thus the method may considered to be a method to confirm or refute a suspicion that NEC is developing in a subject and/or the subject is at risk for NEC. Conversely, the method can also be considered to be a method to confirm or refute a conclusion that a subject is not developing NEC or is not at risk for NEC. In these embodiments the subject may already have one or more symptoms of NEC, but a conclusive diagnosis is not yet possible or NEC has not yet developed fully. The feature "prior to onset of detectable symptoms of NEC" should be construed accordingly.

In other aspects the method may be used to confirm or refute that a subject displaying symptoms that might be indicative of the onset of NEC is developing NEC. In still further embodiments the method may be used to provide information that can contribute to a diagnosis of NEC or rule out a diagnosis of NEC or contribute to the differential diagnosis of diseases and conditions that share symptoms with NEC. Thus, in certain aspects of the invention the collection and/or profiling of the sample occurs before the subject is diagnosed conclusively as having NEC, i.e. the subject is a subject which has not previously been diagnosed as having NEC. An intellectual act of diagnosis is not necessarily required, it is sufficient that the subject has symptoms sufficient to result in conclusive diagnosis were one to be attempted. Thus, in certain aspects of the invention the collection and/or profiling of the sample occurs before full onset of NEC.

Thus, the invention also provides a method for identifying a neonatal subject at risk for NEC, said method comprising (a) profiling the microbiota in a sample from the GI tract of said subject prior to a conclusive diagnosis of NEC and/or prior to full onset of NEC, (b1) comparing said profile to a standard microbiota profile obtained from corresponding samples from neonatal subjects with NEC or subjects which later developed NEC and determining the degree of correlation between said profile and the standard profile(s), and/or (b2) comparing said profile to a standard microbiota profile obtained from corresponding samples from neonatal subjects which did not develop NEC and determining the degree of correlation between said profile and the standard profile, and (c) identifying the subject as being at risk of NEC if significant correlation is observed in (b1) and/or significant correlation is not seen in (b2).

In certain embodiments the subject is identified as being at risk of NEC if a more significant correlation is observed in (b1) than the correlation seen in (b2).

The invention also provides a method of obtaining information relevant to the diagnosis of NEC in a subject at risk for NEC or rule out a diagnosis of NEC subject at risk for NEC, said method having steps (a) to (c) of the above described aspects of the invention.

In these embodiments "prior to" means at least 6 hrs, preferably at least 12, 18 or 24 hrs before detection of symptoms, full onset of NEC and/or conclusive diagnosis. More preferably "prior" means at least 1 day, e.g. at least 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19 or 20 days before detection of symptoms and/or conclusive diagnosis.

The GI tract sample is a sample from the subject that contains detectable levels of microorganisms. By "detectable" it is meant that the presence of microorganisms can be confirmed with the detection technique being employed. Of course, some are more sensitive than others. In preferred embodiments the GI tract sample is a sample that has been collected from the subject as soon as microorganisms become detectable therein, or shortly thereafter, e.g. at least 6 hrs, preferably at least 12, 18 or 24 hrs after detection threshold has been reached. More preferably at least 1 day, e.g. at least 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19 or 20 days after detection threshold has been reached.

The age of the subject at which said sample will be collected therefrom will depend on the type of sample being collected and the individual circumstances of the subject. In certain embodiments the sample will be collected at least 6 hrs, preferably at least 12, 18 or 24 hrs after birth. More preferably at least 1 day, e.g. at least 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19 or 20 days after birth. In other embodiments the age of the subject at which said sample will be collected therefrom will be less than 30 days old, e.g. less than 25, 20, 19, 18, 17, 16, 15, 14, 13, 12, 11, 10, 9, 8, 7, 6, 5, 4, 3, 2 or 1 days old.

Put differently, when the sample is collected, the subject may be 12, 18 or 24 hrs old, more preferably at least 1 day, e.g. at least 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19 or 20 days old, and not displaying detectable symptoms of NEC or having been diagnosed conclusively as having NEC. The subject preferably may be 12, 18 or 24 hrs old, more preferably at least 1 day, e.g. at least 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19 or 20 days old, but is at an age that is least 6 hrs, preferably at least 12, 18 or 24 hrs, preferably at least 1 day, e.g. at least 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19 or 20 days before detection of symptoms and/or conclusive diagnosis.

Alternatively viewed, when the sample is collected the subject will be between 6 hrs and 30 days old, e.g. 12 hrs-25 days, or 1-20, 2-19, 3-18, 4-17, 5-16, 6-15, 7-14, 8-13, 9-12, 10-11, 1-15, 2-15, 3-15, 4-15, 5-15, 6-15, 7-15, 8-15, 9-15, 10-15, 11-15, 12-15, 13-15, 14-15, 1-10, 2-10, 3-10, 4-10, 5-10, 6-10, 7-10, 8-10, 9-10, 1-8, 2-8, 3-8, 4-8, 5-8, 6-8, 7-8, 1-6, 2-6, 3-6, 4-6, 5-6, 4-5, 4-6, 4-7, 4-8, 4-9, 4-10, 4-11, 4-12, 4-13, 4-14, 4-15, 4-16, 4-17, 4-18, 4-19, 4-20, 6-7, 6-8, 6-9, 6-10, 6-11, 6-12, 6-13, 6-14, 6-15, 6-16, 6-17, 6-18, 6-19, 6-20, 8-9, 8-10, 8-11, 8-12, 8-13, 8-14, 8-15, 8-16, 8-17, 8-18, 8-19, 8-20, 10-11, 10-12, 10-13, 10-14, 10-15, 10-16, 10-17, 10-18, 10-19, 10-20 days old and not displaying detectable symptoms of NEC or having been diagnosed conclusively as having NEC, or is at least 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19 or 20 days before detection of symptoms and/or conclusive diagnosis.

The skilled man would be capable of diagnosing NEC from his common general knowledge. As mentioned above, diagnosis typically occurs as a result of the detection of any or all of the following: increased abdominal girth, visible intestinal loops, obvious abdominal distension and decreased bowel sounds, change in stool pattern, hematochezia, a palpable abdominal mass, erythema of the abdominal wall, respiratory failure, decreased peripheral perfusion, and circulatory collapse. Certain of these symptoms are detectable with radiological techniques or ultrasonography. Some of these symptoms are shared with other diseases and medical conditions but the skilled man would also be able to rule out differential diagnoses from his common general knowledge.

The subject may be any neonatal subject, i.e. either term or preterm (premature) neonates. "Preterm"/"premature" refers to an infant that is born prior to the full gestation period, i.e. 38 weeks from the date of assumed fertilisation. A "term" infant is an infant that is born at or after 38 weeks from assumed fertilisation. The subject will commonly be a preterm subject that was born less than 38 weeks from assumed fertilisation, e.g. less than 37, 36, 35, 34, 33, 32, 31 or 30 weeks from assumed fertilisation. Preferably the subject was born less than 38 weeks from assumed fertilisation, e.g. less than 34, 33, 32, 31 or 30 weeks from assumed fertilisation.

The methods of the invention are typically in vitro methods performed using any sample taken from the GI tract. The GI tract, also referred to as the digestive tract or alimentary canal (and which terms may be used interchangeably with GI tract) is the continuous series of organs beginning at the mouth and ending at the anus. Specifically this sequence consists of the mouth, the pharynx, the oesophagus, the stomach, the duodenum, the small intestine, the large intestine and the anus. These organs can be subdivided into the upper GI tract, consisting of the mouth, pharynx, oesophagus, stomach, and duodenum, and the lower GI tract, consisting of the jejunum, the ileum (together the small intestine), the cecum, the colon, the rectum (together the large intestine) and the anus.

A GI tract sample of use in the invention may include, but is not limited to any fluid or solid taken from the lumen or surface of the GI tract or any sample of any of the tissues that form the organs of the GI tract. Thus the sample may be any luminal content of the GI tract (e.g. stomach contents, intestinal contents, mucus, meconium and faeces/stool, or combinations thereof) as well as samples obtained mechanically from the GI tract e.g. by swab, rinse, aspirate or scrape of a GI tract cavity or surface or by biopsy of a GI tract tissue/organ. Faecal or meconium samples are preferred. The sample can also be obtained from part of a GI tract tissue/organ which has been removed surgically. The sample may be a portion of the excised tissue/organ. In embodiments where the sample is a sample of a GI tract tissue/organ the sample may comprise a part of the mucosa, the submucosa, the muscularis externa, the adventitia and/or the serosa of the GI tract tissue/organ. Such tissue samples may be obtained by biopsy during an endoscopic procedure. Preferably the sample is obtained from the lower GI tract, i.e. from the jejunum, the ileum, the cecum, the colon, the rectum or the anus. More preferably the sample is a mucosal or luminal sample. Faecal and meconium samples may be collected by the swab, rinse, aspirate or scrape of the rectum or anus or, most simply, collection after defecation.

The sample may be used in the methods of the invention in the form in which it was initially retrieved. The sample may also have undergone some degree of manipulation, refinement or purification before being used in the methods of the invention. Thus the term "sample" also includes preparations thereof, e.g. relatively pure or partially purified starting materials, such as semi-pure preparations of the above mentioned samples. The term "sample" also includes preparations of the above mentioned samples in which the RNA of which, including the 16S rRNA, has undergone reverse transcription.

The purification may be slight, for instance amounting to no more than the concentration of the solids, or cells, of the sample into a smaller volume or the separation of cells from some or all of the remainder of the sample. Representative cell isolation techniques are described in WO98/51693 and WO01/53525.

In other embodiments the invention uses a preparation of the nucleic acid from the above mentioned samples, preferably a preparation in which the nucleic acids have been labelled. Such preparations include reverse transcription products and/or amplification products of such samples or nucleic acid preparations thereof. Preferably the predominant nucleic acid of the nucleic acid preparation is DNA.

Techniques for the isolation of nucleic acid from samples, including complex samples, are numerous and well known in the art and described at length in the literature. The techniques described in WO98/51693 and WO01/53525 can also be employed to prepare nucleic acids from the above mentioned samples. These preparations include relatively pure or partially purified nucleic acid preparations.

The term "microbiota profile" is intended to mean any representation of the relative amounts of the various microorganisms, preferably prokaryotes, e.g. bacteria, in the sample and/or simply a representation of the presence or absence of certain microorganisms in the sample. The profile may amount to a representation of all microorganisms in the sample, but typically technical constraints will mean that only a selection of the microorganisms present will be represented in the profile as a consequence of technical limits on detection sensitivity, or the inherent specificity of the tools (e.g. oligonucleotide probes or antibodies) that are selected for use in the preparation of the profile. It is envisaged that the successful execution of the method of the invention will not require a selection of particular types of microorganisms to be represented in a particular profile and instead it will be sufficient merely to ensure that the techniques used to prepare the test profiles and the standard profiles are the same and thus are able to give a true comparison between the profiles obtained from the samples. In other words, the constituent microorganisms of the profiles are not necessarily important so long as the profiles permit direct comparison, e.g. the samples are collected from corresponding sites in the GI tract and in the same manner, they are stored and manipulated in the same way and analysed in the same manner.

The profiles may be qualitative, partially quantitative, semi quantitative or fully quantitative representations of the relative amounts of the various microorganisms, preferably prokaryotes, in a sample. Partially quantitative, semi quantitative or fully quantitative profiles are preferred as these permit quantification of the risk a subject has of developing NEC in accordance with the method of the invention. The profiles may be in the form of raw data or may be in a form that has been exposed to one or more rounds of data analysis, e.g. PLS-DA. The profiles may be graphical representations of raw data or processed data.

Thus, in certain embodiments step (a) of the method of the invention can be considered to be a step of determining the relative amounts of a plurality of different types of microorganisms in said sample.

In certain embodiments the relative amounts of at least 2, e.g. at least 3, 4, 5, 6, 7, 8, 9, 10 11, 12, 13, 14, 15, 20, 25, 30, 40 or at least 50 different types of microorganisms are determined. By "different types" it is meant different genera or different species of microorganism, preferably different genera. By way of example, suitable bacteria genera to analyse in accordance with the method of the invention include genera from the Actinobacteria phylum, *Anaerococcus, Bacteroides, Bifidobacterium, Enterobacter, Enterococcus, Finegoldia*, genera from the Firmicutes phylum (e.g. *Clostridium*, genera from the Bacillales order, *Enterococcus, Lactobacillus*, genera from the Lactobacillales order, *Staphylococcus*) genera from the Gammaproteobacteria subgroup, *Gemella, Haemophilus, Klebsiella, Listeria, Megasphaera*, genera from the Proteobacteria phylum, *Pseudomonas, Raoultella, Kluyvera, Salmonella, Serratia, Shigella, Escherichia, Streptococcus, Veillonella*.

In certain embodiments at least the following different genera of microorganism are targeted for analysis: *Haemophilus, Salmonella, Clostridium*, genera from the Bacillales order (e.g. *Bacillus, Listeria* and *Staphylococcus*) *Enterococcus, Lactobacillus, Pseudomonas*, genera from the Gammaproteobacteria subgroup, *Klebsiella, Raoultella, Kluyvera, Serratia* and *Megasphaera*.

The skilled man would be aware of many techniques that would enable him to determine the amounts of microorganisms in a sample and/or simply confirm the presence or absence of certain microorganisms in a sample. Any and all of such techniques may be used in accordance with the invention.

In preferred embodiments the microbial nucleic acid in the sample is analysed as the means by which the amounts of microorganisms in the GI tract sample are determined. Typically this is done by analysing the sample to determine the amounts of nucleotide sequences characteristic of specific microorganisms that are present in the sample. Thus, in this embodiment step (a) of the method of the invention comprises a step of determining the amounts of a plurality of nucleotide sequences each of which is characteristic of a different type of microorganism present in said sample. This is currently considered to represent the most sensitive, accurate and quickest way to obtain such information. Numerous approaches may be used.

In one embodiment the analysis involves the use of oligonucleotides that are capable of hybridising to nucleotide sequences present in the nucleic acids of microorganisms that are characteristic of particular microorganisms or groups of microorganisms, e.g. those types of microorganisms described above. Through a large number of techniques, a selection of which will be described later in more detail, these oligonucleotides can provide information on the amounts of the characteristic nucleotide sequences to which they hybridise in the sample and thus information on the amounts of the microorganisms containing those sequences in the sample.

Typically, in the practice of the invention, a plurality of oligonucleotides will be used in order to detect sequences characteristic of a plurality of different microorganisms. However, single oligonucleotides may be designed which can hybridise to nucleotide sequences characteristic of more than one type of microorganism, or which can hybridise to a plurality of sequences, each of which is characteristic of a single microorganism. Accordingly, a unique oligonucleotide is not necessarily required for each different microorganism being targeted for analysis. Thus, in some embodiments only a single oligonucleotide need be used in the method of the invention.

For the sake of clarity, in the following discussion, the oligonucleotide(s) used to determine the amounts of the plurality of different types of microorganisms targeted for analysis are referred to as an "oligonucleotide probe set".

The probe set may be used to interrogate a single sample as a complete entity (all probes interrogate the sample in a single reaction), but in other embodiments multiple aliquots of the sample may be exposed to one or more members of the probe set in parallel reactions. By running sufficient numbers of aliquots of the sample in parallel, a single sample can be interrogated by the entire probe set in the course of an experiment even if the probe set is not used as a complete entity in the same reaction. Preferably the probe set is applied to the sample as a complete, or substantially complete, entity.

Therefore, in certain embodiments of the invention the step of profiling the microbiota in the sample comprises (i) contacting the sample with an oligonucleotide probe set as defined above;

(ii) subjecting the sample and the probe set to conditions which allow hybridisation of the probes to their target nucleotide sequences within nucleic acid molecules in said sample; and (iii) for each oligonucleotide in said probe set, determining the amount of its target nucleotide sequence that is present in said sample, and (iv) determining the profile of the microbiota in the sample from the relative amounts of said target sequence.

Nucleotide sequences characteristic of particular microorganisms or groups of microorganisms can be found in the genome of microorganisms and in the RNA of microorganisms. The nucleotide sequences of 23S and 16S rRNA genes (and consequently 23S and 16S rRNA itself) offer a well characterised and rich source of such characteristic sequences. 16S rRNA gene sequences are a preferred source. Other examples of suitable sources include the spacer region between 23S and 16S rRNA genes, and the sequences for ATPases, nucleic acid elongation factors and other housekeeping genes. The skilled man can easily identify suitable sequences from the scientific literature, publicly accessible databases and other resources, or by sequencing the nucleic acids of microorganisms himself.

In certain embodiments the oligonucleotide probe set may comprise an oligonucleotide comprising a nucleotide sequence selected from those recited in Table 1 and Table 2, or a sequence capable of hybridising to any nucleotide sequence recited in Table 1 and Table 2 under conditions of high stringency.

In other embodiments the oligonucleotide probe set comprises oligonucleotides comprising a nucleotide sequence selected from at least 2, preferably at least 3, 4, 5, 6, 7, 8, 9, 10, 11, 15, 20, 25, 30 or 35 of those recited in Table 1 and Table 2, or a sequence capable of hybridising to any nucleotide sequence recited in Table 1 and Table 2 under conditions of high stringency.

In other embodiments the oligonucleotide probe set comprises (a) an oligonucleotide comprising a nucleotide sequence selected from CACATGAGCGTCAGTACATTCC (SEQ ID NO 1), the sequence complementary thereto (GGAATGTACTGACGCTCATGTG; SEQ ID NO 36) or a sequence capable of hybridising to either sequence under conditions of high stringency;

(b) an oligonucleotide comprising a nucleotide sequence selected from TGTTGTGGTTAATAACCGCAGCAATTGA (SEQ ID NO 2), the sequence complementary thereto (TCAATTGCTGCGGTTATTAACCACAACA; SEQ ID NO 37) or a sequence capable of hybridising to either sequence under conditions of high stringency;

(c) an oligonucleotide comprising a nucleotide sequence selected from GGACAACGCTTGCCAC (SEQ ID NO 3), the sequence complementary thereto (GTGGCAAGCGTTGTCC; SEQ ID NO 38) or a sequence capable of hybridising to either sequence under conditions of high stringency;

(d) an oligonucleotide comprising a nucleotide sequence selected from ACCGCTACACAGGAAATT (SEQ ID NO 4), the sequence complementary thereto (AATTTCCTGTGTAGCGGT; SEQ ID NO 39) or a sequence capable of hybridising to either sequence under conditions of high stringency;

(e) an oligonucleotide comprising a nucleotide sequence selected from GGAATTCCACTTTCCTCTCCGATACT (SEQ ID NO 5), the sequence complementary thereto (AGTATCGGAGAGGAAAGTGGAATTCC; SEQ ID NO 40) or a sequence capable of hybridising to either sequence under conditions of high stringency;

(f) an oligonucleotide comprising a nucleotide sequence selected from GCACCTGTCTCACAGTT (SEQ ID NO 6), the sequence complementary thereto (AACTGTGAGACAGGTGC; SEQ ID NO 41) or a sequence capable of hybridising to either sequence under conditions of high stringency (g) an oligonucleotide comprising a nucleotide sequence selected from GTTTCCAATGACCCTCC (SEQ ID NO 7), the sequence complementary thereto (GGAGGGTCATTGGAAAC; SEQ ID NO 42) or a sequence capable of hybridising to either sequence under conditions of high stringency or an oligonucleotide comprising a nucleotide sequence selected from CGTCAGGGGACGTT (SEQ ID NO 8), the sequence complementary thereto (AACGTCCCCTGACG; SEQ ID NO 43) or a sequence capable of hybridising to either sequence under conditions of high stringency;

(h) an oligonucleotide comprising a nucleotide sequence selected from CCCCGCTGAAAGTG (SEQ ID NO 9), the sequence complementary thereto (CACTTTCAGCGGGG; SEQ ID NO 44) or a sequence capable of hybridising to either sequence under conditions of high stringency;

(i) an oligonucleotide comprising a nucleotide sequence selected from CACTCCTCAAGGGAACAA (SEQ ID NO 10), the sequence complementary thereto (TTGTTCCCTTGAGGAGTG; SEQ ID NO 45) or a sequence capable of hybridising to either sequence under conditions of high stringency; and (j) an oligonucleotide comprising a nucleotide sequence selected from AGCGTATTAAGCTCACCA (SEQ ID NO 11), the sequence complementary thereto (TGGTGAGCTTAATACGCT; SEQ ID NO 46) or a sequence capable of hybridising to either sequence under conditions of high stringency.

Any and all combinations of the various individual options for each component are specifically contemplated and hereby disclosed.

The probe set may, and typically will, comprise more than one copy of each selected oligonucleotide probe species.

Additional oligonucleotide probes may be present in the probe set, e.g. SEQ ID NOs 12-35 and 47-70 as listed in Table 2. Any and all combinations of the various individual options are specifically contemplated and hereby disclosed. Preferably the additional oligonucleotide probes will contribute to the information on the content of GI tract microbiota that the probe set may provide. This may be by the additional probes providing positive information on the microbiota of the GI tract or by providing information that may act as a control for one or more of the other probes in the probe set or standardised information that might permit quantification of the information obtained from one or more of the other probes in the probe set. The additional probes may target the same or different bacteria as one or more of the probes of the probe set defined above.

In the embodiments of the invention in which the oligonucleotide probe set comprises the oligonucleotides specifically disclosed above, the target nucleotide sequences for SEQ ID NOs 1 to 35 are the sequences fully complementary thereto, i.e. SEQ ID NOs 36 to 70, respectively. Likewise, the target nucleotide sequences for SEQ ID NOs 36 to 70 are the sequences fully complementary thereto, i.e. SEQ ID NOs 1 to 35, respectively. In certain embodiments the target nucleotide sequences for SEQ ID NOs 1 to 35 are the sequences of SEQ ID NOs 36 to 70, respectively, with a G residue immediately 5' of said nucleotide sequence. Likewise, the target nucleotide sequences for SEQ ID NOs 36 to 70 are the sequences of SEQ ID NOs 1 to 35, respectively with a C residue immediately 3' of said nucleotide sequence.

The amount of target sequence can be determined by any convenient means and many such means will be familiar to the skilled man. This can be a partially, semi- or fully quantitative measurement, but can also be a qualitative (or relative) measure in which results for each target are simply compared to one another without numerical values being affixed. As discussed later, in some embodiments quantitative measurement is performed and the data obtained is analysed with statistical techniques in order to determine the statistically significant features of the microbiota profile, and the correlation between profiles.

In one embodiment the amount of each target sequence is determined by using the oligonucleotides of the probe set with labels attached thereto that will allow detection by direct means or indirect means. In other words the oligonucleotide probes are used simply as conventional oligonucleotide probes. Suitable labels are described below. After contact of such probes with the sample, under conditions which allow for hybridisation of the probes to their target sequences, and typically following a step (or steps) to remove unbound labelled oligonucleotides and/or non-specifically bound oligonucleotides, the strength of the signal from the label of each probe emanating from the sample under investigation (i.e. the amount of label bound to the sample) will be proportional to the amount of hybridised oligonucleotide, and therefore its target sequence. In preferred embodiments the label is selected such that it is detectable only when the probe is hybridised to its target. In such embodiments, the need to remove the unbound probe is lessened.

Any convenient means may be used to remove any unbound or non-specifically bound probes, for instance with one or more washing steps (e.g. with water or a buffered solution which may contain formamide and/or a detergent), electrophoresis, centrifugation, capture onto solid supports, chromatography or any combination thereof. Suitable solid supports are described below. In another embodiment the probes may carry a binding moiety, or the label may be a binding moiety, that will allow manipulation of the probes and any part of the sample hybridised thereto. Suitable binding moieties are discussed below.

Thus, in certain embodiments of the invention the step of profiling the microbiota in the sample comprises (i) contacting the sample with an oligonucleotide probe set as defined above, wherein each oligonucleotide has a label attached thereto;

(ii) subjecting the sample and the probe set to conditions which allow hybridisation of the probes to their target nucleotide sequences within nucleic acid molecules in said sample; and (iii) for each labelled oligonucleotide in said probe set, determining the amount of said label bound to said sample by determining the strength of the signal from the label emanating from the sample, and (iv) determining the profile of the microbiota in the sample from the relative amounts of each said label bound to the sample.

The amount of each label bound to the sample is indicative of the amount of the target sequence for that labelled oligonucleotide in said sample.

In a preferred embodiment the method will comprise a step between steps (i) and (ii) in which unbound oligonucleotide and/or non-specifically bound oligonucleotide is removed.

In another embodiment the amount of each target nucleotide sequence present in the sample is determined by using an oligonucleotide probe set, in particular those sets comprising oligonucleotide probes which comprise nucleotide sequences selected from SEQ ID NOs 1 to 35, e.g. SEQ ID NOs 1 to 11, as a set of probes which are labelled only when hybridised to their target sequences. In some embodiments the oligonucleotides of the probe set may already carry a label that is different to the label used to selectively label the probes. The strength of the signal from the selectively labelled probes emanating from the sample under investigation (i.e. the amount of labels bound to the sample) will be proportional to the amount of hybridised oligonucleotide and in turn the amount of target sequence.

As mentioned previously, depending on the conditions employed, this can be a partially, semi- or fully quantitative measurement, but can also be a qualitative (or relative) measure in which results for each target sequence are simply compared to one another without numerical values being affixed.

Conveniently, selective labelling may be achieved using labelled nucleotides, i.e. by incorporation into the oligonucleotide probe of a nucleotide carrying a label. In other words, selective labelling may occur by chain extension of the oligonucleotide probe using a polymerase enzyme which incorporates a labelled nucleotide, preferably a labelled dideoxynucleotide (e.g. ddATP, ddCTP, ddGTP, ddTTP, ddUTP) more preferably labelled ddCTP, most preferably a fluorescently labelled, e.g. TAMRA labelled, ddCTP, or a biotin labelled ddCTP. This approach to the detection of specific nucleotide sequences is sometimes referred to as primer extension analysis. Suitable primer extension analysis techniques are well known to the skilled man, e.g. those techniques disclosed in WO99/50448, the contents of which are incorporated herein by reference. Suitable labels are described below.

In the case of oligonucleotide probes terminating with SEQ ID NOs. 1 to 35 at their 3', the label will preferably be a labelled ddCTP, e.g. a TAMRA or biotin labelled ddCTP. Most preferably in this embodiment the probe set of the invention will comprise oligonucleotides consisting of SEQ ID NOs 1 to 35 and the label will be a labelled ddCTP, e.g. a TAMRA or biotin labelled ddCTP.

Detection of the labelled probes can be by any means convenient for the label being used. The skilled man would be able to devise suitable methods based on his selection of labels. In preferred embodiments, the labels are fluorescent labels (e.g. TAMRA) and in such embodiments the fluorescently labelled probes can be detected and, if required, quantified using a device that can measure the intensity (or strength) of fluorescent signals. A biotin label may be detected indirectly by exposing the label to streptavidin, or another biotin-binding molecule, which carries a detectable moiety, e.g. a colorimetric, chemiluminescent, chromogenic, radioactive or fluorescent label. In some embodiments, detection will occur after the labelled probes have undergone manipulation to remove, at least partially, contaminants (e.g. unlabelled probes, excess label, and other reagents used in the labelling reaction). Again, the skilled man would be very familiar with techniques which can achieve this, by way of example mention is made of electrophoresis (e.g. gel, e.g. capillary gel electrophoresis), centrifugation, chromatography and filtration based techniques, capture onto solid supports, or any combination thereof.

In other preferred embodiments the selectively labelled oligonucleotide probes are detected after a step in which the oligonucleotide probes from the selective labelling step (i.e. labelled and unlabelled), or the selectively labelled oligonucleotide probes only, are hybridised to nucleotide sequences that are partially, or preferably fully, complementary to the oligonucleotide probes.

Conveniently, the complementary nucleotide sequences can be provided on one of more solid supports, e.g. those described below.

Thus, in certain embodiments of the invention the step of profiling the microbiota in the sample comprises (i) contacting the sample with an oligonucleotide probe set as defined above, (ii) subjecting the sample and the probe set to conditions which allow hybridisation of the probes to their target nucleotide sequences within nucleic acid molecules in said sample;

(iii) selectively labelling the oligonucleotide probes of the probe set when hybridised to their target nucleotide sequence;

(iv) determining the amount of each labelled oligonucleotide probe produced in step (iii), and (v) determining the profile of the microbiota in the sample from the amounts of each labelled oligonucleotide probe.

The amount of each labelled oligonucleotide probe is indicative of the amount of the target sequence for that labelled oligonucleotide in said sample.

In some embodiments, step (iv) comprises hybridisation of the oligonucleotide probes from the labelling step to sequences complementary to those oligonucleotides.

In a further embodiment the amount of each target nucleotide sequence present in the sample is determined by labelling the nucleic acids in the sample prior to the step of contacting the sample with the oligonucleotide probe set. Simply by assessing the amount of labelled nucleic acid hybridising to the probes of the probe set the amount of the target nucleotide sequence for each oligonucleotide probe that is present in said sample can be determined.

In these embodiments those regions containing the target sequences for the oligonucleotides of the probe set, e.g. 23S or 16S rRNA or 23S or 16S rDNA sequences, or nucleic acids comprising said sequences are labelled prior to contact with the probe set. Suitable labels are discussed below. Conveniently labelling occurs when the nucleic acids in the sample are amplified and/or reverse transcribed prior to contact with the probe set as discussed in more detail below. Conveniently the nucleic acids are labelled by the incorporation of labelled nucleotides during a nucleic acid amplification reaction and/or a reverse transcription reaction.

In further embodiments both the oligonucleotides of the probe set and the nucleic acids in the sample as described above are labelled with moieties that provide a signal only when in close proximity, e.g. when the probes are hybridised to their target sequences in the nucleic acid.

In another embodiment the amount of each target nucleotide sequence present in the sample is determined by using the oligonucleotides of the probe set as primers in one or more nucleic acid amplification reactions, e.g. a multiplex amplification reaction. If the appropriate conditions are selected, such a reaction can be performed such that the amount of amplification product obtained for each oligonucleotide of the probe set will be proportional to the amount of each target nucleotide sequence present in the sample. Thus, the amount of product the amplification reaction provides for each oligonucleotide of the probe set is a measure of the amount of that oligonucleotide that hybridises to the sample from the subject under investigation and is in turn proportional to the amount of target sequence for that oligonucleotide in the sample and so is proportional to the amount of microorganism that that oligonucleotide is designed to target in the sample. Accordingly, the amount of amplification product can be used to determine the amounts of these microorganisms in the sample.

As mentioned previously, depending on the conditions employed, this can be a partially, semi- or fully quantitative measurement, but can also be a qualitative (or relative) measure in which results for each target sequence are simply compared to one another without numerical values being affixed.

Amplification can be achieved by any convenient primer-dependent nucleic acid amplification reaction. Most conveniently the polymerase chain reaction (PCR) will be used, although the skilled man would be aware of other techniques. For instance LAR/LCR, SDA, Loop-mediated isothermal amplification and nucleic acid sequence based amplification (NASBA)/3SR (Self-Sustaining Sequence Replication) may be used.

Many variations of PCR have been developed, for instance Real Time PCR (also known as quantitative PCR, qPCR), hot-start PCR, competitive PCR, and so on, and these may all be employed where appropriate to the needs of the skilled man.

In one basic embodiment of the invention using a PCR based amplification the oligonucleotides of the probe set are contacted with a reaction mixture containing the sample, a suitable set of second primers to form a set of working primer pairs and free nucleotides in a suitable buffer under conditions which allow hybridisation. Thermal cycling of the resulting mixture in the presence of a DNA polymerase results in amplification of the target sequences for each oligonucleotide, i.e. sequences characteristic of the microorganism the oligonucleotides of the probe set of the invention are designed to target.

Optimal performance of the PCR process is influenced by choice of temperature, time at temperature, and length of time between temperatures for each step in the cycle. A typical cycling profile for PCR amplification is (a) 15 minutes of DNA melting at 95° C.; (b) 30 seconds of primer annealing at 50-65° C.; (c) 90 seconds of primer extending at 68-72° C.; (d) 30 seconds of DNA melting at 95° C.; and steps (b)-(d) are repeated as many times as necessary to obtain the desired level of amplification.

Modifications of the basic PCR method such as qPCR (Real Time PCR) have been developed that can provide quantitative information on the template being amplified. Numerous approaches have been taken although the two most common techniques use double-stranded DNA binding fluorescent dyes or selective fluorescent reporter probes.

Double-stranded DNA binding fluorescent dyes, for instance SYBR Green, associate with the amplification product as it is produced and when associated the dye fluoresces. Accordingly, by measuring fluorescence after every PCR cycle, the relative amount of amplification product can be monitored in real time. Through the use of internal standards and controls, this information can be translated into quantitative data on the amount of template at the start of the reaction.

The fluorescent reporter probes used in qPCR are commonly sequence specific oligonucleotides, typically RNA or DNA, that have a fluorescent reporter molecule at one end and a quencher molecule at the other (e.g. the reporter molecule is at the 5' end and a quencher molecule at the 3' end or vice versa). The probe is designed so that the reporter is quenched by the quencher. The probe is also designed to hybridise selectively to particular regions of complementary sequence which might be in the template. If these regions are between the annealed PCR primers the polymerase, if it has exonuclease activity, will degrade (depolymerise) the bound probe as it extends the nascent nucleic acid chain it is polymerising. This will relieve the quenching and fluorescence will rise. Accordingly, by measuring fluorescence after every PCR cycle, the relative amount of amplification product can be monitored in real time. Through the use of internal standard and controls, this information can be translated into quantitative data.

Thus, in certain embodiments of the invention the step of profiling the microbiota in the sample comprises (i) contacting the sample with an oligonucleotide probe set as defined above;

(ii) subjecting the sample and the probe set to conditions which allow hybridisation of the probes to their target nucleotide sequences within nucleic acid molecules in said sample;

(iii) performing a primer-dependent nucleic acid amplification reaction;

(iv) for each oligonucleotide in the probe set determining the amount of amplification product produced therefrom in said primer-dependent nucleic acid amplification reaction, and (v) determining the profile of the microbiota in the sample from the amounts of said product for each oligonucleotide.

The amount of said product for each oligonucleotide is indicative of the amount of the target sequence for each oligonucleotide in the sample.

In a preferred embodiment step (i) will also comprise contacting the sample with a set of oligonucleotides that are capable of functioning with the oligonucleotide set of the invention in a nucleic acid amplification reaction, e.g. PCR, to produce an amplification product for each oligonucleotide of the probe set, assuming a suitable template is present in the sample. In this embodiment, when paired with a second set of suitable amplification primers, the oligonucleotides comprising SEQ ID NOs 1 to 35 will act as forward primers and oligonucleotides comprising SEQ ID NOs 36 to 70 will act as reverse primers.

In this embodiment the method may involve a plurality of primer dependent nucleic acid amplifications being run in parallel, with each reaction involving a single probe, or one or more multiplex primer dependent nucleic acid amplifications being run with two or more probes being used in the same reaction.

The amplification product from each oligonucleotide may be detected, and amounts of amplification product can be determined, by any convenient means. To some extent feasible techniques will be dictated by the number of oligonucleotides of the probe set that are used in each amplification reaction (e.g. whether the reaction is a multiplex reaction or not or the extent of multiplexing). The skilled man would be able to select appropriate techniques.

A vast number of techniques are routinely employed as standard laboratory techniques and the literature has descriptions of more specialised approaches. At its most simple the amount of amplification product may be detected or determined by visual inspection of the reaction mixture at the end of the reaction or at a desired timepoint. Typically the amplification product will be resolved with the aid of a label that may be preferentially bound to the amplification product. Typically a dye substance, e.g. a colorimetric, chromogenic, fluorescent or luminescent dye (for instance ethidium bromide or SYBR green) is used. In other embodiments a labelled oligonucleotide probe that preferentially binds the amplification product, in particular a probe that binds preferentially to substantially all of the individual amplified nucleic acids in the amplification product, is used. A suitable probe might be based on the nucleotide sequence of one or more of SEQ ID NOs 1 to 70. Suitable labels for the probe are discussed below. In some embodiments the probe may be provided in an unlabelled form with labelling occurring after preferential binding to the amplification product, or preferential binding to substantially all of the individual amplified nucleic acids in the amplification product.

However, in some cases a nucleic acid precipitant (e.g. salt and/or alcohol) can simply be used to cause the amplification product to come out of solution and be visible without labelling.

To aid visualisation the components of amplification product can be dispersed in or on a solid support, for instance by electrophoresis (e.g. using agarose or polyacrylamide gels), chromatography (e.g. HPLC, TLC, affinity, gel filtration) or filtration, or a combination thereof, prior to or after contact with the label.

Depending on the label used detection can be made more accurate by using widely available detection technologies, e.g. radiation sensitive films and digital imaging technologies in combination with computer assisted image analysis, photometers, fluorometers, colorimeters, scintillation counters, and the like.

Preferably the amplification product is separated from the remainder of the amplification reaction before being contacted by the label, e.g. in the form of a labelled oligonucleotide probe. This may be by any convenient means, for instance with one or more washing steps (e.g. with water or a buffered solution which may contain formamide and/or a detergent), electrophoresis, centrifugation, capture onto nucleic acid binding solid supports, chromatography or any combination thereof. Conveniently, the probe can be provided on a solid support thereby effecting separation of the amplification product from the remainder of the amplification reaction in a single step. In another embodiment the probe may carry a binding moiety, or the label may be a binding moiety, that will allow manipulation of the probe and any amplification product hybridised thereto. Suitable binding moieties are discussed below.

Preferably any unbound label, e.g. in the form of a labelled oligonucleotide probe, will be separated from the amplification product before the detection step. This can be by any convenient means, for instance with one or more washing steps (e.g. with water or a buffered solution which may contain formamide and/or a detergent), electrophoresis, centrifugation, capture onto solid supports, chromatography or any combination thereof. Suitable solid supports are described above.

If the amplification method used is itself quantitative, e.g. amplification methods in which internal standards and controls are incorporated (for instance qPCR) the method of this aspect of the invention can also provide quantitative data. In these embodiments the method can even affix a numerical value to the amount of target sequence present in the sample and thus the amount of the microorganisms containing the target sequence in the sample. One such internal standard would be to amplify one or more (e.g. at least 2, 3, 5, or 10) samples which have known amounts of the microorganisms targeted by the oligonucleotides of the probe set or known quantities of target sequence under the same conditions as the test sample to provide a standard curve plotting amount of amplification product against number of organisms or amount of target sequence. The amount of amplification product obtained in the test sample can then be translated into a numerical value for the amount of target sequence and/or microorganisms containing the target sequence of the oligonucleotides of the probe set in the sample.

In other embodiments, the progress of the amplification reaction can be followed in real-time and the amplification profile can be compared with amplification profiles from samples which have known amounts of the microorganisms targeted by the oligonucleotides of the probe set or of known quantities of target sequence. In other embodiments the cycle threshold ($C_T$) can be used to calculate the amount of target sequence and therefore the amounts of the microorganisms targeted by the oligonucleotides of the probe set in the sample. In all qPCRs there is a threshold at which the fluorescence of the amplification product is detected above background. The cycle at which this threshold is crossed is the $C_T$. In the exponential phase of the reaction the quantity of DNA theoretically doubles every cycle and so relative amounts of DNA can be calculated between samples by comparing $C_T$ values falling in the exponential phase. If the comparison is made with samples with a known quantity of template, the quantity of template in the test sample can be calculated and the amount of target sequence of the oligonucleotides of the probe set present in the sample and thus the amount of microorganisms containing the target sequence of the oligonucleotides of the probe set in the sample can be determined.

A combination of one or more the above described techniques for determining the amount of target nucleotide sequence may be used in the practice of the invention.

In the above described embodiments of the method of the invention there may also be preceding steps in which the nucleic acid in the sample is amplified. Preferably the amplification reaction performed on the sample will be universal, or substantially universal, in that the nucleic acid to be amplified, e.g. the region of 16S rRNA or 16S rDNA incorporating the target sequences for the oligonucleotides described above in terms of a SEQ ID NO, is amplified from all, or at least substantially all, microorganisms that might be present in a sample. The term "amplification from substantially all microorganisms present in a sample" refers to the number of different species of microorganisms in the sample that will have the nucleic acid to be amplified, amplified. Thus, in this embodiment the nucleic acid to be amplified is amplified from at least one representative of substantially all species of microorganisms in the sample.

For those embodiments of the invention in which oligonucleotides that hybridise to target sequences in 16S rRNA are used, conveniently this universal amplification may be performed using a forward primer targeting the conserved region between V2 and V3 (e.g. that described in Nadkarni et al., 2002. Microbiology 148, 257-266) with a reverse primer targeting the 3'-end of the 16S rRNA gene (e.g. that described in Weisburg et al., 1991, J Bacteriol 173, 697-703). In other embodiments this universal amplification may be performed using a primer pair having the sequences TCC TAC GGG AGG CAG CAG (SEQ ID NO 71), also referred to as MangalaF-1, and CGG TTA CCT TGT TAC GAC TT (SEQ ID NO 72), also referred to as 16SU1510R. This primer pair is described in more detail in US2011/0104692.

The target nucleotide sequence to be amplified in these embodiments is therefore present in 16S rRNA and the corresponding 16S rRNA gene (rDNA). Thus, reference to the amplification of this target nucleotide sequence is a reference to an increase in the number of nucleic acids that contain that sequence of nucleotides without limitation on the type of nucleic acids containing the nucleotide sequence. Preferably these nucleic acids will be labelled. Typically, the nucleic acid that is formed as the amplification product is DNA, although the nucleotide sequence contained in that nucleic acid will still be the same as that of the target nucleotide sequence, or the complement thereof.

Conveniently, these embodiments of the invention will be performed with 16S rDNA, e.g. a 16S rRNA gene, as the template.

In other embodiments 16S rRNA may be the source of the target nucleotide sequence to be amplified. When a target nucleotide sequence from 16S rRNA is amplified in this embodiment of the method of the invention there will be a step in which an RNA-dependent DNA polymerase catalyses the formation of a DNA molecule complementary to the 16S rRNA template (cDNA). This process is termed "reverse transcription". More specifically the RNA-dependent DNA polymerase catalyses the polymerisation of deoxyribonucleoside triphosphates in a sequence that is complementary (i.e. following Watson-Crick base pairing rules) to a primed template rRNA sequence.

Numerous enzymes have been identified that have the ability to catalyse this reaction and examples include, but are not limited to, HIV reverse transcriptase, AMV reverse transcriptase, M-MLV reverse transcriptase, *C. therm.* polymerase, and Tth polymerase. At its most basic a complete reverse transcription reaction mixture will contain a reverse transcription enzyme, the rRNA template, suitable primers that can bind to the template and from which the reverse transcriptase can begin polymerisation, dNTP's and a suitable buffer. Incubation of the mixture at the working temperature of the reverse transcriptase results in cDNA production.

Upon completion of the reverse transcription reaction the cDNA can be used as the template in the embodiment of the method of the invention described above. The cDNA therefore has a nucleotide sequence that is complementary to the rRNA molecule that was its template. In addition the cDNA has a nucleotide sequence that is the same as a nucleotide sequence contained in one strand of the gene of the rRNA template and the cDNA is complementary to a nucleotide sequence contained in the other strand of the gene of the rRNA template.

As mentioned above, in embodiments of the method of the invention in which nucleic acid is amplified in a preceding step, if 16S rRNA is used as the source of the target nucleotide sequence (as opposed to 16S rDNA, e.g. a 16S rRNA gene) an initial reverse transcription step is required. Reverse transcription linked amplification reactions, in particular PCR, can be "one step" or "two step" processes. In a one step process the components of the reverse transcription reaction and the nucleic acid amplification reaction are present in a single reaction vessel and typically the early reaction conditions are selected to allow the reverse transcription reaction to proceed to completion and reaction conditions are then switched to conditions suitable to allow the nucleic acid amplification reaction to proceed.

In a two step process the components of the reverse transcription reaction are first combined and the reverse transcription reaction is performed. The reverse transcription product is then combined with the components of the amplification reaction and subjected to the amplification reaction. In a "one tube" two step protocol the amplification reaction components are added to the same reaction vessel in which the reverse transcription reaction was performed. In a "two tube" two step protocol the amplification reaction is performed in a fresh reaction vessel.

In other embodiments the microbial proteins in the sample are analysed as the means by which the amounts of microorganisms in the GI tract sample are determined. Typically this is done by analysing the sample to determine the amounts of peptide sequences characteristic of specific microorganisms that are present in the sample. Thus, in this embodiment step (a) of the method of the invention comprises a step of determining the amounts of a plurality of peptide sequences each of which is characteristic of a different type of microorganism in said sample. Numerous approaches may be used.

Conveniently, this analysis takes advantage of interactive proteins/peptides that can bind selectively to peptide sequences characteristic of specific microorganisms. Antibody based technologies which can provide antibodies, antibody fragments and derivatives thereof which can selectively bind to peptide sequences characteristic of specific microorganisms are a classic example of this, however, other technologies are available that have the same functionality as antibodies (e.g. affibodies and those which exploit other proteins that naturally bind to targets in or on microorganisms) and these technologies can also be used. Techniques in which these technologies can be applied to determine the presence or absence of peptide sequences characteristic of specific microorganisms include but are not limited to ELISA, immunoblotting, western blotting, immunocytochemistry, flow cytometry, fluorescence-activated cell sorting and so on. Many variations and specialisations of these techniques will be known to the skilled man and can be employed in the present invention.

Therefore, in certain embodiments of the invention the step of profiling the microbiota in the sample comprises (i) contacting the sample with a set of interactive proteins that can bind selectively to peptide sequences characteristic of specific microorganisms;

(ii) subjecting the sample and the set of interactive proteins to conditions which allow binding of the set of interactive proteins to their target peptide sequences within said sample;

(iii) for each interactive protein in said set, determining the amount of its target peptide sequence that is present in said sample; and (iv) determining the profile of the microbiota in the sample from the relative amounts of said target sequence.

The set of interactive proteins may be used to interrogate a single sample as a complete entity (all interactive proteins interrogate the sample in a single reaction), but in other embodiments multiple aliquots of the sample may be exposed to one or more members of the set of interactive proteins in parallel reactions. By running sufficient numbers of aliquots of the sample in parallel, a single sample can be interrogated by the entire set of interactive proteins in the course of an experiment even if the set of interactive proteins is not used as a complete entity in the same reaction. Preferably the set of interactive proteins is applied to the sample as a complete, or substantially complete, entity.

In another embodiment there are the culture based techniques in which the microorganisms in a sample are grown in culture systems as far as pure colonies and those colonies are then identified/classified taxonomically by tests including, but not limited to nucleic acid, e.g. DNA, sequencing, metabolic testing (e.g. the AP1-20E test strip), immunodetection and nucleic acid detection (e.g. using techniques similar to that described above). Other techniques to identify and classify microorganisms make use of microscopy (e.g. light, electron, confocal, X-ray, infra-red) to identify morphologies and structures in the cells and/or colony that are characteristic of particular microorganisms or groups of microorganisms. Microorganisms can also be identified and classified with techniques involving culture on selective media, i.e. media deficient in one or more nutrients or essential elements or comprising one or more potentially toxic compounds. Identification and classification can be assisted by assessing which media a particular microorganism can survive on. Differential culture media can also be used to provide an indication of the metabolic capabilities of a test colony, e.g. what sugars or amino acids the colony can metabolise or which macromolecule (e.g. starch, cellulose, proteins, DNA) can be broken down by the microorganism. These media usually employ a colour-change type system to show these capabilities in action. Still further techniques for identifying and classifying microorganisms are based on the differential uptake of biological stains by microorganisms. Such stains include, but are not limited to, Gram stain, acid fast stain, endospore stain, Ziehl-Neelsen stain, acridine orange, Bismarck brown, carmine, crystal violet, eosin, acid fuchsine, haematoxylin, Hoechst stain, malachite green, methyl green, methylene blue, neutral blue, Nile red, Nile blue, osmium tetroxide, rhodamine, safranin. A combination of these tests may also be used to accurately and precisely classify the consistent microorganisms in a sample.

It is well known how to employ these culture and detection techniques to achieve at least a degree of quantisation in the results. Thus, in this embodiment step (a) of the method of the invention comprises a step of culturing the microorganisms in a sample and a step of analysing the products of the culture step to determine the amounts of a plurality of different types of microorganisms in said sample.

In another aspect the invention also provides a method for identifying a neonatal subject at risk for NEC, said method comprising (i)(a) comparing the microbiota profile from a sample from the GI tract of a neonatal subject at risk for NEC, said profile having been obtained prior to a conclusive diagnosis of NEC and/or prior to full onset of NEC, to a standard microbiota profile obtained from corresponding samples from neonatal subjects with NEC or subjects which later developed NEC and determining the degree of correlation between said profile and the standard profile(s), and/or (i)(b) comparing the microbiota profile from a sample from the GI tract of a neonatal subject at risk for NEC, said profile having been obtained prior to a conclusive diagnosis of NEC and/or prior to full onset of NEC, to a standard microbiota profile obtained from corresponding samples from neonatal subjects which did not develop NEC and determining the degree of correlation between said profile and the standard profile (b) identifying the subject as being at risk of NEC if significant correlation is observed in (i)(a) and/or significant correlation is not seen in (i)(b). Preferably the subject has not previously been confirmed as being at risk for NEC.

In certain embodiments the subject is identified as being at risk of NEC if a more significant correlation is observed in (i)(a) than the correlation seen in (i)(b).

In an embodiment of this method the microbiota profile under comparison is from a sample from the GI tract of a neonatal subject at risk for NEC, said profile having been obtained prior to the onset of detectable symptoms of NEC.

The invention also provides a method of obtaining information relevant to the diagnosis of NEC in a subject at risk for NEC or rule out a diagnosis of NEC subject at risk for NEC, said method having steps (i)(a) or (i)(b) and (b) of the above described aspects of the invention.

The above discussion of the invention applies mutatis mutandis to these aspects, in particular, but not limited to, the discussion of the preparation of microbiota profiles from samples from the GI tract of neonatal subjects.

The standard microbiota profiles to which the microbiota profiles from the sample under test are compared are prepared in the same way as the microbiota profiles from the sample under test are prepared. The samples are preferably equivalent in terms of their source and the techniques used to collect them and manipulate them. The standard profiles may be a combination of results obtained from multiple subjects, i.e. an average value, or an average of multiple profiles from a single control subject or a single profile from a single control subject. These standards may have been produced some time prior to the analysis of the sample from the subject under investigation and may be provided to the practitioner digitally, e.g. on digital media or via electronic transfer to the user. In other embodiments a system may be in place in which the results obtained from the subject under test contributes to the development of the standard profile.

Data generated using the above mentioned profiling techniques may be analysed using various techniques, from the most basic visual representation (e.g. relating to signal intensity directly from the sample) to more complex data manipulation, which may be quantified and expressed mathematically, to prepare more easily comparable profiles of GI tract microbiota which reflect the interrelationship of the relative amounts of each microorganism in the sample. The raw data thus generated may be manipulated by data processing and statistical methods, particularly those which normalise and standardise the data, and/or convert the data into a more easily comparable model. The skilled man would be aware of suitable statistical techniques to use. Preferably the statistical technique will provide a "value" as an indication that the trend being observed is not a random trend. A statistically significant result, i.e. a result that is not attributable to random variation when compared to its control, will have a P value of <0.05, preferably <0.01, <0.005 or <0.001. Merely by way of example, suitable techniques for measuring statistical significance in the methods of the invention are ANOVA, Mann-Whitney-Wilcoxon (MWW) Test, Kruskal-Wallis Test and Tukey's Honestly Significant Differences (HSD) Test. Many others would be familiar to the skilled man. In some embodiments a permutation test might be appropriate, e.g. that described by Langsrud (2002, Journal Of The Royal Statistical Society Series D 51, 305-317). A suitable modelling approach is PLS-DA; partial least squares discriminant analysis.

The term "to correlate" should be construed broadly and should not be limited to any particular form or technique. In certain embodiments correlating the test profile to a standard profile merely involves determining whether the profiles are similar to one another or determining whether the profiles correspond to one another. This may be a qualitative assessment or it may be quantitative to some extent. The determination of a "significant correlation" usually involves an assessment of the extent to which the profiles are similar to one another or the extent to which the profiles correspond to one another, again this may be qualitative and therefore subjective. In embodiments which are to some extent quantitative these assessments of correlation, e.g. determination of similarity and/or correspondence and extent thereof, can involve data analysis and statistical tests to obtain a more objective measure of correlation (e.g. similarity and/or correspondence) and extent thereof. At a very simple level the skilled man can look at qualitative profiles and form a conclusion that the test profile is more like the standard than not and thus a significant correlation exists. In other more quantitative embodiments the skilled man can use numerical data to make these assessments. In other embodiments the data may be analysed in such a way (e.g. with PLS-DA) that a graphical representation of the data, e.g. a clustering diagram, can be prepared in which test and standard profiles can be visualised as being correlated, e.g. significantly correlated, or not, see Example 1 for instance. Other ways of representing the microbiota profiles and comparing them to one another will be well known to the skilled man. In some embodiments these assessments will be made, completely or in part, by machine, e.g. an automated machine, and the skilled man will need only review the results of the machine-based comparisons. In other embodiments the statistical tests and modelling techniques described above, or others, can be used to inform the skilled man whether or not the correlation is statistically significant. A statistically significant correlation is preferred.

The probe sets described above constitute another aspect of the invention.

The invention also provides an oligonucleotide probe comprising a nucleotide sequence selected from any one of SEQ ID NOs 1-70 or a nucleotide sequence capable of hybridising to said nucleotide sequence under conditions of high stringency. The use of such probes in the products of the invention and in their preparation, and the use of such probes in the methods of the invention are further aspects of the invention. The probes and probe sets defined herein may be used in a method for diagnosing NEC in a subject with NEC or may be used to contribute to the diagnosis of NEC in a subject with NEC. In such methods the microbiota profiling steps and profile comparison and correlation steps will be the same as described previously and all discussion above applies mutatis mutandis to these aspects. The only difference is that the sample will be collected from a neonatal subject that has NEC, but in which a conclusive diagnosis has not yet been made.

In all aspects of the invention described herein references to "the nucleotide sequence of SEQ ID NO X", also include reference to nucleotide sequences capable of hybridising under high stringency conditions to SEQ ID NO X unless the context dictates otherwise.

The oligonucleotides of the probe sets described herein may vary in size depending on which nucleotide sequence they comprise. Generally, the oligonucleotides may be up to 100 nucleotides, preferably up to 80, 60, 50, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11 or up to 10 nucleotides in length. The oligonucleotides of the probe sets described herein may be at least 9, preferably at least 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 60, or at least 80 nucleotides. In certain embodiments, the oligonucleotides of the probe sets described herein may comprise at least 1, 2, 3, 4, 5, 6, 7, 8, 9, 10, 11, 12, 13, 14, 15, 16, 17, 18, 19, 20, 21, 22, 23, 24, 25, 30, 40, 60, or at least 80 nucleotides in addition to the number of nucleotides in whichever sequence of SEQ ID NOs 1 to 70 that is present in the oligonucleotide.

The nucleotides of the oligonucleotides of the probe sets can be any type of nucleotide so long as hybridisation specificity or efficiency and, if necessary, nucleic acid polymerisation efficiency or primer dependent nucleic acid amplification efficiency is not detrimentally effected. The oligonucleotides may therefore be deoxyribonucleotides, ribonucleotides, modifications thereof (e.g. PNA, morpholino, LNA) and mixtures thereof. DNA oligonucleotides and LNA modified DNA oligonucleotides are preferred.

The nucleotides corresponding to SEQ ID NOs 1 to 70 may be found in any part of the oligonucleotide probes so long as the oligonucleotides can hybridise to the complementary target sequence of the SEQ NO under consideration and, if required, can effect a nucleic acid extension reaction. In some embodiments the 3' nucleotide of whichever sequence of SEQ ID NOs 1 to 70 that is present in the oligonucleotide is the 3' nucleotide of the oligonucleotide.

In other embodiments the oligonucleotides consist essentially of a sequence selected from SEQ ID NOs 1 to 70. Thus, the oligonucleotides will have a nucleotide sequence selected from SEQ ID NOs 1 to 70 and 1, 2, 3, 4, or 5 additional nucleotides. In other embodiments the oligonucleotides will consist of a sequence selected from SEQ ID NOs 1 to 70.

Unless otherwise stated, or dictated by specific context, all nucleotide sequences are recited herein 5' to 3' in line with convention in this technical field.

High stringency conditions for hybridisation are defined as 2×SSC/50% formamide at 50° C. for binding conditions and 2×SSC at 65° C. for washing conditions (where SSC=0.15 M NaCl, 0.015 M sodium citrate, pH 7.2).

In preferred embodiments the nucleotide sequences that can hybridise to one of SEQ ID NOs. 1 to 70 under high stringency conditions will hybridise to all, or substantially all, of the nucleotides in the sequences of SEQ ID NOs 1 to 70, e.g. a series of contiguous nucleotides with a number of nucleotides that amounts to at least 50% preferably at least 55, 60, 65, 70, 75, 80, 85, 90 or 95% of the total number of nucleotides in the sequence of the SEQ ID NO under consideration.

Viewed alternatively, nucleotide sequences that can hybridise to the nucleotide sequences of one of SEQ ID NOs. 1 to 35 or 36 to 70 under high stringency conditions may be those nucleotide sequences that correspond to the nucleotide sequence of SEQ ID NOs. 36 to 70 or 1 to 35, respectively but with up to 40% of the bases (adenine, thymine/uracil, guanine, or cytosine) in the nucleotide sequences of SEQ ID NOs. 36 to 70 or 1 to 35, being substituted with a different base. Preferably up to 35, 30, 25, 20, 15, 10 or 5% of the bases will be substituted. Put another way, nucleotide sequences that can hybridise to the nucleotide sequences of one of SEQ ID NOs. 1 to 35 or 36 to 70 under high stringency conditions may be those nucleotide sequences that correspond to the nucleotide sequence of SEQ ID NOs. 36 to 70 or 1 to 35, respectively but with up to 5, 4, 3 or 2 substituted bases or only a single base substitution. The base being substituted into the sequence can be any standard or non-standard, naturally occurring or synthetic base.

Nucleotide sequences that can hybridise to SEQ ID NOs. 1 to 35 or 36 to 70 under high stringency conditions will preferably be 9, 10, 11, 12, 13, 14, 15, 16, 17, 18, 19, 20, 21, 22, 23, 24, 25, 26, 27 or 28 nucleotides in length, and consist of a contiguous part of the nucleotide sequence of SEQ ID 36 to 70 or 1 to 35, respectively, with the above described substitutions.

Preferably the base substitution(s) occur at or near the 5' end of the nucleotide sequence, e.g. in the final 15, 10 or 5 5' nucleotides in the sequence. Put differently, the base substitution(s) preferably do not occur at or near the 3' end of the nucleotide sequence, e.g. in the final 2, 3, 4, 5, 10 or 15 3' nucleotides. In other embodiments the 3' nucleotide will not have a substituted base.

In certain embodiments any of the oligonucleotides of the probe set comprising a nucleotide sequence of any one of SEQ ID NOs 1 to 35 may have a C residue immediately 3' of said nucleotide sequence or any of the oligonucleotides comprising a nucleotide sequence of any of one of SEQ ID NOs 36 to 70 may have a G residue immediately 5' of said nucleotide sequence.

The oligonucleotides described herein, e.g. those of the probe sets described herein, the interactive proteins described herein, e.g. antibodies, antibody fragment or derivatives of antibodies, or the amplification products described herein may be labelled with a moiety to assist with detection or manipulation. A large number of suitable moieties and labelling methods are known in the art and described in the literature. Many moieties can perform both functions. Any detectable or signal-generating molecule or reporter molecule may be used. Convenient labels include colorimetric, chemiluminescent, chromogenic, radioactive and fluorescent labels, but enzymatic (e.g. colorimetric, luminescent, chromogenic) or antibody-based labelling methods or signal-generating systems may also be used. Thus the term "label" as used herein includes not only directly detectable signal-giving or passive moieties, but also any moiety which generates a signal or takes part in a signal generating reaction or that may be detected indirectly in some way. For instance the moiety may be biotin and detection may be indirect via streptavidin carrying a colorimetric, chemiluminescent, chromogenic, radioactive or fluorescent moiety.

The label can, in some embodiments, comprise a plurality of moieties that contributes to the overall detectable output of the label. By varying the identity and/or the relative proportions of these moieties, a wide palette of unique labels can be constructed. For instance, a plurality of dyes, e.g. luminescent (e.g. bioluminescent, chemiluminescent, photoluminescent, radioluminescent, sonoluminescent, etc.) which combine to give a unique electromagnetic spectral signature upon excitation may be used. By varying the proportions of the selected dyes further differentiation in the spectral signature can be achieved. Signatures based on the absorption of certain wavelengths of electromagnetic radiation are also envisaged.

Fluorescein or other fluorescently labelled nucleotides are particularly suitable for incorporation into the oligonucleotides and amplification products, and allow detection directly by fluorescence or indirectly by antibody interactions. These are commercially available. Nucleic acids can be labelled by e.g. [$^{35}$S], [$^{3}$H] or [$^{32}$P]. Any suitable binding moiety may be used as a label, for instance an antibody fragment, His-tag, biotin or streptavidin. These may be incorporated in the form of labelled nucleotides.

Some or all of the oligonucleotides described herein, e.g. those of the probe sets described herein, may be provided immobilised on one or more solid supports for use in the invention. The incorporation of a 5 residue poly C tail at the 5' end of the oligonucleotide can be used to assist in immobilisation. In other embodiments the oligonucleotides described herein, e.g. those of the probe sets described herein, may be immobilised on one or more solid supports prior to use. Single or preferably multiple copies are attached to said solid supports, e.g. 10 or more, e.g. at least 100 copies of each unique probe are present.

One or more oligonucleotide probes of the probe sets described herein, each of a certain sequence, may be associated with separate solid supports which together form a set of probes immobilised on multiple solid supports, e.g. one or more oligonucleotide probes of the probe set may be immobilized on multiple beads, membranes, filters, biochips etc. The solid supports of the different parts of the probe set are conveniently physically associated although the signals associated with each probe (generated as described hereinafter) must be separately determinable.

Alternatively, the probes may be immobilised on discrete portions of the same solid support, e.g. each oligonucleotide probe of a certain sequence, typically in multiple copies, may be immobilised to a distinct and discrete portion or region of a single chip, plate, filter or membrane, e.g. to generate an array.

A combination of such techniques may also be used, e.g. several solid supports may be used which each carry several probes of differing sequence immobilised thereon.

The expression "solid support" shall mean any solid material able to bind oligonucleotides, e.g. by hydrophobic, ionic or covalent interaction.

"Immobilisation" as used herein refers to reversible or irreversible association of the probes to said solid support. If reversible, the probes remain associated with the solid support for a time sufficient for methods of the invention to be carried out.

Suitable immobilising supports to which the oligonucleotides described herein can be attached are known in the art and include any of the well known supports or matrices which are currently widely used or proposed for immobilisation, separation etc. of oligonucleotides. Such materials include, but are not limited to, any synthetic organic polymer such as polystyrene, polyvinylchloride, polyethylene; or nitrocellulose and cellulose acetate; or agarose, cellulose, alginate, teflon or latex; or tosyl activated surfaces; or glass or nylon or any surface carrying a group suited for covalent coupling of nucleic acids. These may take the form of particles, sheets, gels, filters, membranes, fibres, capillaries, chips or microtitre strips, slides, tubes, plates or wells etc. Methods of immobilising or attaching oligonucleotides to solid supports are likewise known in the art. Particularly preferred are DNA chips (microchips, glass chips) now common in molecular biology procedures. In other embodiments membrane strips on to which the oligonucleotides may be spotted and then UV cross-linked may be used. Alternatively, attachment may be performed indirectly by the use of an attachment moiety carried on the oligonucleotide and/or solid support. Thus for example, a pair of affinity binding partners may be used, such as avidin, streptavidin or biotin, DNA or DNA binding protein (e.g. either the lac I repressor protein or the lac operator sequence to which it binds), antibodies (which may be mono- or polyclonal), antibody fragments or the epitopes or haptens of antibodies. In these cases, one partner of the binding pair is attached to (or is inherently part of) the solid support and the other partner is attached to (or is inherently part of) the nucleic acid molecules.

As used herein an "affinity binding pair" refers to two components which recognise and bind to one another specifically (i.e. in preference to binding to other molecules).

Attachment of appropriate functional groups to the solid support may be performed by methods well known in the art, which include for example, attachment through hydroxyl, carboxyl, aldehyde or amino groups which may be provided by treating the solid support to provide suitable surface coatings. Solid supports presenting appropriate moieties for attachment of the binding partner may be produced by routine methods known in the art.

Attachment of appropriate functional groups to the oligonucleotides described herein may be performed by ligation or introduced during synthesis or amplification, for example using primers carrying an appropriate moiety, such as biotin or a particular sequence for capture.

In certain embodiments, each oligonucleotide of a certain sequence may be associated with a separate solid support, e.g. a bead or a microsphere, having a particular label such that a population, or plurality of populations, of particles having the same label and the same probe immobilised thereon is formed. Detection of a hybridisation event occurring on a particle with a particular label will provide information on the sequence of the oligonucleotide involved in that event.

The particles may be labelled in any convenient way, e.g. using one or more of the labels described above. In one embodiment the particle label will not be or comprise an oligonucleotide, or a nucleic acid, or a labelled oligonucleotide or labelled nucleic acid. Conveniently the particulate solid support of these embodiments will be labelled with a dye, e.g. a luminescent (e.g. bioluminescent, chemiluminescent, photoluminescent, radioluminescent, sonoluminescent, etc.) dye, or a plurality of dyes (or proportions thereof) which combine to give a unique electromagnetic spectral signature upon excitation. Signatures based on the absorption of certain wavelengths of electromagnetic radiation are also envisaged.

Conveniently the dye will be fluorescent, e.g. comprise red or infrared fluorophores, e.g. phycoerythrin.

The label may be immobilised on and/or in the particle, e.g. by direct covalent binding to the substrate of the particle or it may be bound to another molecule which is in turn immobilised on and/or in the particle. The label may also be incorporated into and/or onto the particle by non-covalent means, e.g. by entrapment, absorption or adsorption of the molecules making up the label in or on the substrate of the particle, or by entrapment in void(s) within the substrate and/or on its surface.

In other embodiments the particle comprises nanoparticles on which and/or in which the label has been immobilised or incorporated.

The label can be applied to the particle after it is produced, or the label may be incorporated or immobilised into and/or onto the particle during its production, e.g. during the cross-linking of a polymeric substrate.

Preferably the label of the oligonucleotide(s) will be distinguishable from the label of the particle(s). In preferred embodiments the label of the particles will be detectable at the same time as the label of the oligonucleotide (s). Preferably the labelled particles will also be magnetic, e.g. paramagnetic or superparamagnetic.

Suitable particulate solid supports are manufactured by Luminex Corp. See for instance WO01/13120, WO01/13119, WO97/14028 and WO99/19515, the contents of which are incorporated herein by reference. Further particles which may be used in the working on the invention are provided in U.S. Pat. Nos. 4,267,234, 4,267,235, 4,552,812, 4,677,138, 5,194,300, 4,774,189, 5,073,498, 4,717,655, 5,723,218, 5,326,692, 5,716,855, 5573909 and U.S. Pat. No. 5,786,219, the contents of which are incorporated herein by reference. Other suitable solid supports are manufactured by Illumine, Inc. See for instance WO00/39587, WO 01/18524, WO01/59432 and WO02/00336 the contents of which are incorporated herein by reference.

Preferably the support is magnetic (preferably paramagnetic or superparamagnetic), e.g. magnetic particles, for instance magnetic beads.

In other embodiments none of the oligonucleotides are used in immobilised form, and in general this is preferred.

The above discussed embodiments relating to solid support bound oligonucleotide probes for use in accordance with the invention applies mutatis mutandis, allowing for inherent technical differences, to solid support bound interactive proteins of use in the invention.

In a further aspect the invention provides kits comprising the one or more of the probes or probe sets as defined herein.

In a further aspect the invention provides the use of the probe set defined herein in the manufacture of the kits as defined herein.

The kits of the invention may be designed for use in the methods of the invention and may comprise further components. Each component may be provided in a separate compartments or vessels. Where convenient and practical, mixtures of components could be provided. The components may be provided in dry, e.g. crystallised, freeze dried or lyophilised, form or in solution, typically such liquid compositions will be aqueous and buffered with a standard buffer such as Tris, HEPES, etc.

The kit may also be provided with instructions for using the kit, or with directions for how instructions may be obtained.

The additional components can be any of the various components that may be used to put the methods of the invention into effect, e.g. any component discussed above.

Further components might optionally be further oligonucleotides that selectively hybridise to target nucleic acids indicative of any other disease or medical condition, particularly conditions associated with the gastrointestinal microbiota and which may accordingly be used in a manner similar to the oligonucleotides of the invention to provide information relevant to a diagnosis of any other disease of medical condition, particularly conditions associated with the gastrointestinal microbiota. These oligonucleotides may be considered a part of the probe set of the invention.

The invention will be further described with reference to the following non-limiting Examples in which:

FIG. 1 shows a representation of PLS-DA models generated from the signal outputs obtained when the probe set and array described in Table 3 was used to interrogate samples obtained at various timepoints after birth from 3 infants that developed NEC and 6 infants that did not develop NEC. *=NEC Subject; ▼=non NEC subject. Figures by each data point represent: Patient ID (age before NEC diagnosis) age when sample taken. The data underlying the represented models is recited in Table 4.

Figure 2:
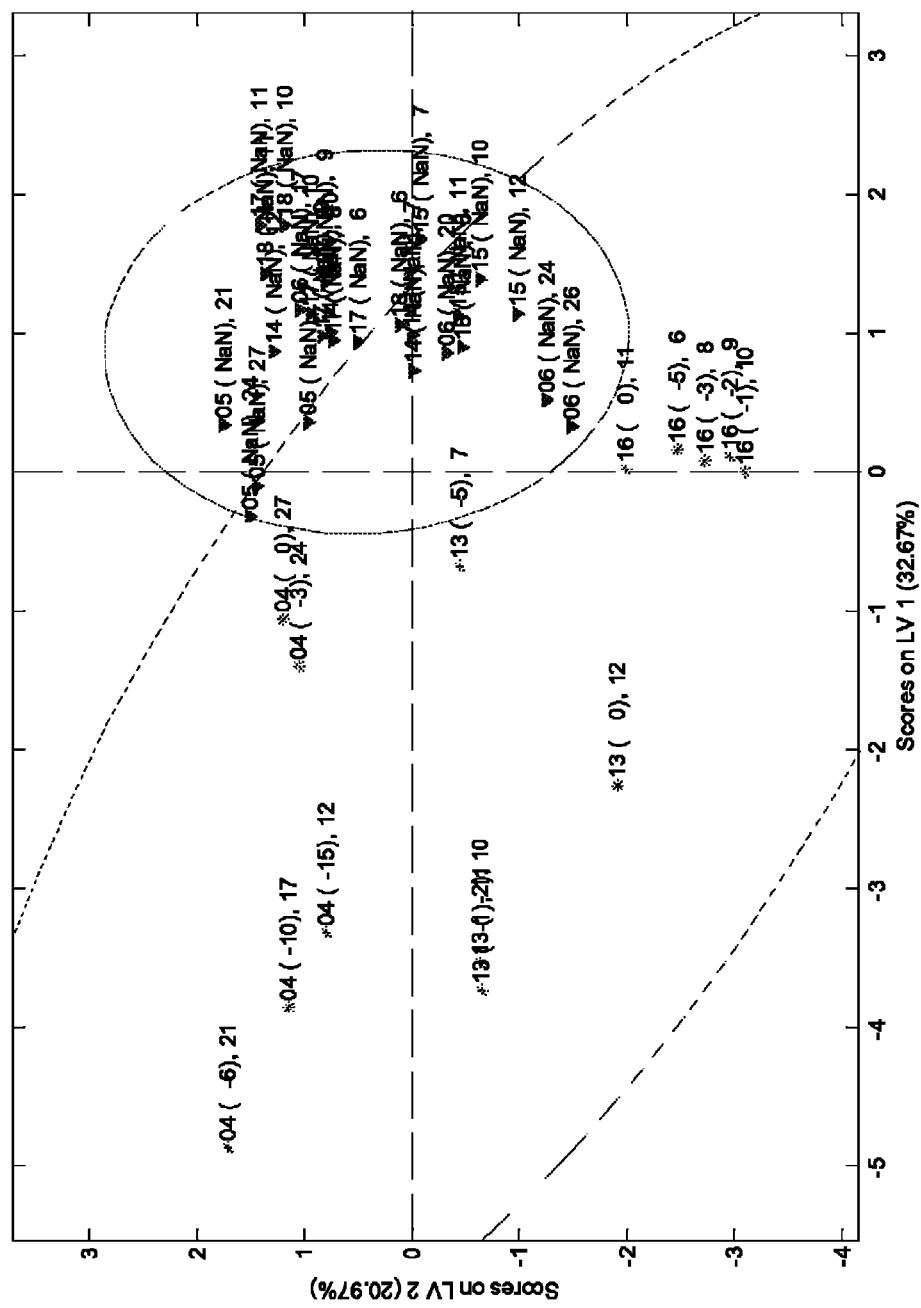

FIG. 2 shows a representation of PLS-DA models generated from the signal outputs obtained when the probe set and array described in Table 3 was used to interrogate samples obtained at various timepoints after birth from 3 infants that developed NEC and 6 infants that did not develop NEC. *=NEC Subject; ▼=non NEC subject. Figures by each data point represent: Patient ID (age before NEC diagnosis) age when sample taken. The data underlying the represented models is recited in Table 4.

TABLE 1

| Probe sequence | SEQ ID NO | Internal Designation | Target bacteria |
|---|---|---|---|
| CACATGAGCGTCAGTACATTCC | SEQ ID NO 1 | IG0008 | *Haemophilus* |
| GGAATGTACTGACGCTCATGTG | SEQ ID NO 36 | | *Haemophilus* |
| TGTTGTGGTTAATAACCGCAGCAATTGA | SEQ ID NO 2 | IG0011 | *Salmonella* |
| TCAATTGCTGCGGTTATTAACCACAACA | SEQ ID NO 37 | | *Salmonella* |
| GGACAACGCTTGCCAC | SEQ ID NO 3 | IG0023 | Firmicutes (Clostridia, Bacillales, *Enterococcus*, *Lactobacillus*) |
| GTGGCAAGCGTTGTCC | SEQ ID NO 38 | | Firmicutes (Clostridia, Bacillales, *Enterococcus*, *Lactobacillus*) |
| ACCGCTACACAGGAAATT | SEQ ID NO 4 | IG0039 | *Pseudomonas* |
| AATTTCCTGTGTAGCGGT | SEQ ID NO 39 | | *Pseudomonas* |
| GGAATTCCACTTTCCTCTCCGATACT | SEQ ID NO 5 | IG0044 | *Megasphaera* |
| AGTATCGGAGAGGAAAGTGGAATTCC | SEQ ID NO 40 | | *Megasphaera* |
| GCACCTGTCTCACAGTT | SEQ ID NO 6 | IG0056 | *E. coli*, *Klebsiella* |
| AACTGTGAGACAGGTGC | SEQ ID NO 41 | | *E. coli*, *Klebsiella* |
| GTTTCCAATGACCCTCC | SEQ ID NO 7 | IG0168 | *Enterococcus* |
| GGAGGGTCATTGGAAAC | SEQ ID NO 42 | | *Enterococcus* |
| CGTCAGGGGACGTT | SEQ ID NO 8 | IG0171 | *Enterococcus* |
| AACGTCCCCTGACG | SEQ ID NO 43 | | *Enterococcus* |
| CCCCGCTGAAAGTG | SEQ ID NO 9 | IG0181 | *Klebsiella pneumoniae* |
| CACTTTCAGCGGGG | SEQ ID NO 44 | | *Klebsiella pneumoniae* |
| CACTCCTCAAGGGAACAA | SEQ ID NO 10 | IG0195 | *Raoultella*, *Kluyvera* |
| TTGTTCCCTTGAGGAGTG | SEQ ID NO 45 | | *Raoultella*, *Kluyvera* |
| AGCGTATTAAGCTCACCA | SEQ ID NO 11 | IG0204 | *Serratia* |
| TGGTGAGCTTAATACGCT | SEQ ID NO 46 | | *Serratia* |

TABLE 2

| Probe sequence | SEQ ID NO | Internal Designation | Target bacteria |
|---|---|---|---|
| ACGCTTGCACCCT | SEQ ID NO 12 | IG0005 | Proteobacteria |
| AGGGTGCAAGCGT | SEQ ID NO 47 | | Proteobacteria |
| CGATCCGAAAACCTTCTTCACT | SEQ ID NO 13 | IG0012 | Firmicutes (Lactobacillales, *Clostridium perf.*, *Staphylococcus*) |
| AGTGAAGAAGGTTTTCGGATCG | SEQ ID NO 48 | | Firmicutes (Lactobacillales, *Clostridium perf.*, *Staphylococcus*) |
| CACTCTCACACCCGTT | SEQ ID NO 14 | IG0020 | *Streptococcus sanguinis* |
| AACGGGTGTGAGAGTG | SEQ ID NO 49 | | *Streptococcus sanguinis* |
| CCGTCAAGGGACAAG | SEQ ID NO 15 | IG0021 | *Listeria* |
| CTTGTCCCTTGACGG | SEQ ID NO 50 | | *Listeria* |
| GTTGCTCGGTCAGACTT | SEQ ID NO 16 | IG0022 | *Streptococcus pneumoniae* |
| AAGTCTGACCGAGCAAC | SEQ ID NO 51 | | *Streptococcus pneumoniae* |
| CGTGGCTTTCTGATTAGGTA | SEQ ID NO 17 | IG0024 | *Staphylococcus* |
| TACCTAATCAGAAAGCCACG | SEQ ID NO 52 | | *Staphylococcus* |
| TGCTTATTCAACGGGTAAACT | SEQ ID NO 18 | IG0027 | *Bifidobacterium longum* |
| AGTTTACCCGTTGAATAAGCA | SEQ ID NO 53 | | *Bifidobacterium longum* |
| CGTAGGCGGTTCGTCGCGT | SEQ ID NO 19 | IG0028 | Actinobacteria |
| ACGCGACGAACCGCCTACG | SEQ ID NO 54 | | Actinobacteria |
| CGGTGCTTATTCGAAAGGTACACT | SEQ ID NO 20 | IG0030 | *Bifidobacterium breve* |
| AGTGTACCTTTCGAATAAGCACCG | SEQ ID NO 55 | | *Bifidobacterium breve* |
| AGAGCTTTACGAACCGAAAT | SEQ ID NO 21 | IG0042 | *Gemella* |
| ATTTCGGTTCGTAAAGCTCT | SEQ ID NO 56 | | *Gemella* |
| CGGCAGTCTCTCATGAGTT | SEQ ID NO 22 | IG0051 | *Veillonella* |
| AACTCATGAGAGACTGCCG | SEQ ID NO 57 | | *Veillonella* |

TABLE 2-continued

| Probe sequence | SEQ ID NO | Internal Designation | Target bacteria |
|---|---|---|---|
| CCGCTACACATGGAGTT | SEQ ID NO 23 | IG0053 | Lactobacilli |
| AACTCCATGTGTAGCGG | SEQ ID NO 58 | | Lactobacilli |
| CACTAGGAATTCCGCTCTCCTCTC | SEQ ID NO 24 | IG0058 | Clostridium difficile |
| GAGAGGAGAGCGGAATTCCTAGTG | SEQ ID NO 59 | | Clostridium difficile |
| CAATCGGAGTTCTTCGTGATATCTAAG | SEQ ID NO 25 | IG0060 | Bacteroides |
| CTTAGATATCACGAAGAACTCCGATTG | SEQ ID NO 60 | | Bacteroides |
| GCACCACCTGTCACT | SEQ ID NO 26 | IG0063 | Staphylococcus epidermidis |
| AGTGACAGGTGGTGC | SEQ ID NO 61 | | Staphylococcus epidermidis |
| GTTAAACAGTTTCCCAAGCGTA | SEQ ID NO 27 | IG0079 | Streptococcus mitis |
| TACGCTTGGGAAACTGTTTAAC | SEQ ID NO 62 | | Streptococcus mitis |
| CACCTGTCACTTCTGCT | SEQ ID NO 28 | IG0081 | Streptococcus agalactiae |
| AGCAGAAGTGACAGGTG | SEQ ID NO 63 | | Streptococcus agalactiae |
| AGGCGGAGTGTTTATTG | SEQ ID NO 29 | IG0095 | Anaerococcus prevotii |
| CAATAAACACTCCGCCT | SEQ ID NO 64 | | Anaerococcus prevotii |
| GCTTCCTCCTCTGGTAC | SEQ ID NO 30 | IG0103 | Clostridium sporogenes |
| GTACCAGAGGAGGAAGC | SEQ ID NO 65 | | Clostridium sporogenes |
| CGATACGAATACCTTCTTCGTT | SEQ ID NO 31 | IG0107 | Finegoldia magna |
| AACGAAGAAGGTATTCGTATCG | SEQ ID NO 66 | | Finegoldia magna |
| TCAACCTGGGAACTGCATCTGATA | SEQ ID NO 32 | IG0133 | Shigella, E. coli |
| TATCAGATGCAGTTCCCAGGTTGA | SEQ ID NO 67 | | Shigella, E. coli |
| TCTCGCGAGGTTG | SEQ ID NO 33 | IG0163 | Clostridium butyricum |
| CAACCTCGCGAGA | SEQ ID NO 68 | | Clostridium butyricum |
| CCCCCCTCTACAAGACT | SEQ ID NO 34 | IG0178 | Enterobacter |
| AGTCTTGTAGAGGGGGG | SEQ ID NO 69 | | Enterobacter |
| CGACTCGTTGTACCAG | SEQ ID NO 35 | IG0197 | Streptococcus (parasang., oralis, genomsp) |
| CTGGTACAACGAGTCG | SEQ ID NO 70 | | Streptococcus (parasang., oralis, genomsp) |

EXAMPLE 1

Sample Preparation and PCR Amplification

Fecal samples collected from infants during the first few weeks of life were supplied by the Beth Israel Deaconess Medical Center, Harvard Medical School, Boston, Mass. Samples were obtained from three infants that developed NEC and six infants that did not develop NEC.

Feces were collected from the infant's napkin and stored immediately at −18° C. at home before transported to permanent storage at −80° C. until further analysis. Mechanical lysis was used for cell disruption, and an automated magnetic bead-based method was used for DNA purification.

We combined the use of a forward primer targeting the conserved region between V2 and V3 (Nadkarni et al., 2002. Microbiology 148, 257-266.) with a reverse primer targeting the 3'-end of the 16S rRNA gene (Weisburg et al., 1991, J Bacteriol 173, 697-703). We used 1.5 U HotFirePol (Solis Biodyne, Tartu, Estonia), 1×B2 buffer (Solis Biodyne), 2.5 mM $MgCl_2$ (Solis Biodyne), 200 μM dNTP (Thermo Fisher Scientific, Waltham, USA), 0.2 μM of each forward and reverse primer and approximately 10 to 50 ng template in a total volume of 25 μl. The amplification protocol included a 15 min activation stage at 95° C., followed by 30 cycles with 30 sec denaturation at 95° C., 30 sec annealing at 55° C. and 90 sec extension at 72° C. A final elongation for 7 min at 72° C. was included for completion of all the PCR products.

Design of the GA-Map NEC Assay

The GA-map assay is based on the single nucleotide extension principle (SNupE) in combination with microarray hybridization (Rudi et al., 1998, Appl Environ Microbiol 64, 2639-2643)

For probe construction we used a combined dataset consisting of a total of 3580 16S rRNA gene sequences (Palmer et al., 2007, PLoS Biology 5, e177; Rudi et al., 2007, Appl Environ Microbiol 73, 2727-2734), in addition to a set of known pathogens.

A four-step process was used in designing the probes. 1) First, a set of target and non-target groups based on a coordinate classification system was defined. 2) The next step was to identify probes that satisfy the criteria of target detection and non-target exclusion. This was based on a combined criterion of hybridization and labelling. All probes were designed with minimum Tm of 60° C. for the target group, while the non-target should have a Tm of <30° C., or the absence of a cytosine as the nucleotide adjacent to the 3'-end of the probe. All probes satisfying the criteria were identified. 3) Then the potential cross-labelling or self-labelling probes were evaluated, in addition to the potential for cross hybridization on the array. 4) Finally, by combining the knowledge about target/ non-target groups and compatibility for each of the probes, final arrays were designed using a hierarchical approach.

The probes or the probe set used in this Example are recited in Table 3. Two universal 16S rRNA gene probes (16SUniv and 16SUniv2; SEQ ID NOs 73 and 74, respectively) were included in the probe set to measure the total abundance of bacterial DNA in the sample. One additional probe was added in the hybridization step: a 1:4 mixture of pre-labelled and unlabelled hybridization control probe (HYC01; SEQ ID NO 75). HYC01 is used to measure efficiency of the hybridization step on the slide and to normalize the probe signals between slides. The microarrays used in the GA map NEC assay were produced by Arraylt (Arraylt, Sunnyvale, USA). One glass slide contains 24 separate identical microarrays, and oligonucleotides complementary to the probes of the probe set were spotted in triplicates on each array (also recited in Table 3). Furthermore, the probe set also included two non-binding control probes (NBC2 and NBC4; SEQ ID NOs 76 and 77, respectively).

TABLE 3

| Probe ID | Target bacteria | Sequence of Probe Set for Primer Extension Analysis | SEQ ID NO | Sequence of oligonucleotide spotted onto array (i.e. complement of probe) with 5 residue 5' polyC tail not shown | SEQ ID NO |
|---|---|---|---|---|---|
| IG0005 | Proteobacteria | ACGCTTGCACCCT | 12 | AGGGTGCAAGCGT | 47 |
| IG0008 | Haemophilus | CACATGAGCGTCAGTACATTCC | 1 | GGAATGTACTGACGCTCATGTG | 36 |
| IG0011 | Salmonella | TGTTGTGGTTAATAACCGCAGCAATTGA | 2 | TCAATTGCTGCGGTTATTAACCACAACA | 37 |
| IG0012 | Firmicutes (Lactobacillales, Clostridium perf., Staphylococcus) | CGATCCGAAAACCTTCTTCACT | 13 | AGTGAAGAAGGTTTTCGGATCG | 48 |
| IG0020 | Streptococcus sanguinis | CACTCTCACACCCGTT | 14 | AACGGGTGTGAGAGTG | 49 |
| IG0021 | Listeria | CCGTCAAGGGACAAG | 15 | CTTGTCCCTTGACGG | 50 |
| IG0022 | Streptococcus pneumoniae | GTTGCTCGGTCAGACTT | 16 | AAGTCTGACCGAGCAAC | 51 |
| IG0023 | Firmicutes (Clostridia, Bacillales, Enterococcus, Lactobacillus) | GGACAACGCTTGCCAC | 3 | GTGGCAAGCGTTGTCC | 38 |
| IG0024 | Staphylococcus | CGTGGCTTTCTGATTAGGTA | 17 | TACCTAATCAGAAAGCCACG | 52 |
| IG0027 | Bifidobacterium longum | TGCTTATTCAACGGGTAAACT | 18 | AGTTTACCCGTTGAATAAGCA | 53 |
| IG0028 | Actinobacteria | CGTAGGCGGTTCGTCGCGT | 19 | ACGCGACGAACCGCCTACG | 54 |
| IG0030 | Bifidobacterium breve | CGGTGCTTATTCGAAAGGTACACT | 20 | AGTGTACCTTTCGAATAAGCACCG | 55 |
| IG0039 | Pseudomonas | ACCGCTACACAGGAAATT | 4 | AATTTCCTGTGTAGCGGT | 39 |
| IG0042 | Gemella | AGAGCTTTACGAACCGAAAT | 21 | ATTTCGGTTCGTAAAGCTCT | 56 |
| IG0044 | Megasphaera | GGAATTCCACTTTCCTCTCCGATACT | 5 | AGTATCGGAGAGGAAAGTGGAATTCC | 40 |
| IG0051 | Veillonella | CGGCAGTCTCTCATGAGTT | 22 | AACTCATGAGAGACTGCCG | 57 |
| IG0053 | Lactobacilli | CCGCTACACATGGAGTT | 23 | AACTCCATGTGTAGCGG | 58 |
| IG0056 | E. coli, Klebsiella | GCACCTGTCTCACAGTT | 6 | AACTGTGAGACAGGTGC | 41 |
| IG0058 | Clostridium difficile | CACTAGGAATTCCGCTCTCCTCTC | 24 | GAGAGGAGAGCGGAATTCCTAGTG | 59 |
| IG0060 | Bacteroides | CAATCGGAGTTCTTCGTGATATCTAAG | 25 | CTTAGATATCACGAAGAACTCCGATTG | 60 |
| IG0063 | Staphylococcus epidermidis | GCACCACCTGTCACT | 26 | AGTGACAGGTGGTGC | 61 |
| IG0079 | Streptococcus mitis | GTTAAACAGTTTCCCAAGCGTA | 27 | TACGCTTGGGAAACTGTTTAAC | 62 |
| IG0081 | Streptococcus agalactiae | CACCTGTCACTTCTGCT | 28 | AGCAGAAGTGACAGGTG | 63 |
| IG0095 | Anaerococcus prevotii | AGGCGGAGTGTTTATTG | 29 | CAATAAACACTCCGCCT | 64 |
| IG0103 | Clostridium sporogenes | GCTTCCTCCTCTGGTAC | 30 | GTACCAGAGGAGGAAGC | 65 |
| IG0107 | Finegoldia, magna | CGATACGAATACCTTCTTCGTT | 31 | AACGAAGAAGGTATTCGTATCG | 66 |
| IG0133 | Shigella, E. coli | TCAACCTGGGAACTGCATCTGATA | 32 | TATCAGATGCAGTTCCCAGGTTGA | 67 |
| IG0163 | Clostridium butyricum | TCTCGCGAGGTTG | 33 | CAACCTCGCGAGA | 68 |

TABLE 3-continued

| Probe ID | Target bacteria | Sequence of Probe Set for Primer Extension Analysis | SEQ ID NO | Sequence of oligonucleotide spotted onto array (i.e. complement of probe) with 5 residue 5' polyC tail not shown | SEQ ID NO |
|---|---|---|---|---|---|
| IG0168 | Enterococcus | GTTTCCAATGACCCTCC | 7 | GGAGGGTCATTGGAAAC | 42 |
| IG0171 | Enterococcus | CGTCAGGGGACGTT | 8 | AACGTCCCCTGACG | 43 |
| IG0178 | Enterobacter | CCCCCCTCTACAAGACT | 34 | AGTCTTGTAGAGGGGGG | 69 |
| IG0181 | Klebsiella pneumoniae | CCCCGCTGAAAGTG | 9 | CACTTTCAGCGGGG | 44 |
| IG0195 | Raoultella | CACTCCTCAAGGGAACAA | 10 | TTGTTCCCTTGAGGAGTG | 45 |
| IG0197 | Streptococcus (parasang., oralis, genomsp) | CGACTCGTTGTACCAG | 35 | CTGGTACAACGAGTCG | 70 |
| IG0204 | Serratia | AGCGTATTAAGCTCACCA | 11 | TGGTGAGCTTAATACGCT | 46 |
| NBC2 | Non-binding control | AGGAAGGAAGGAAGGAAGGG | 76 | CCCTTCCTTCCTTCCTTCCT | 78 |
| NBC4 | Non-binding control | TCCTAGTGACGCCGTCGA | 77 | TCGACGGCGTCACTAGGA | 79 |
| 16SUniv | Binding to all 16S | CGTATTACCGCGGCTGCTGGCA | 73 | TGCCAGCAGCCGCGGTAATACG | 80 |
| 16SUniv2 | Binding to all 16S | GTATTACCGCGGCTGCTGG | 74 | CCAGCAGCCGCGGTAATAC | 81 |
| HYC01 | Hybridisation control | GTAGCATTCGATTCGGGCAA | 75 | TTGCCCGAATCGAATGCTAC | 82 |

Primer Extension and Hybridisation to Array

Before the labelling reaction the 16S PCR-products (amplified as described above) were treated with 3 U Exonuclease I (New England Biolabs, Ipswich, USA) and 8 U Shrimp Alkaline Phosphatase (USB, Cleveland, USA) at 37° C. for 2 hours and inactivated at 80° C. for 15 min. The ExoSAP treated PCR-products were then quantified using Kodak Molecular Imaging Software (Version 4.0) based on pictures from gel electrophoresis. A 1 KB DNA Ladder (N3232, New England Biolabs) with specified concentrations was included on all gels. Based on the quantification from the gel images the PCR products were diluted to an equal concentration of 50 ng/µl per sample and approximately 100 ng template was used in the following labelling reaction: In a total reaction volume of 10 µl 2.5 U HOT TERMIPol (Solis Biodyne), 1× buffer C (Solis Biodyne), 4 mM $MgCl_2$ (Solis Biodyne), 0.4 µM ddCTP-tamra (Jena Bioscience, Jena, Germany) and 2.9 µM probe set (Table 3). The labelling protocol included a 12 min activation stage at 95° C., followed by 10 cycles with 20 sec denaturation at 96° C. and 35 sec annealing at 60° C. Samples were randomly picked to examine reproducibility. These samples were processed twice starting from the labelling reaction. Furthermore, as a test of the quantitative range of the assay PCR-products from pure cultures from 5 different species (listed in Table 3) was diluted from $10^0$-$10^{-4}$ and included in the labelling reaction and down-stream array analysis.

The arrays were pre-hybridized to prevent background signal by soaking the glass-slides in BlockIt (ArrayIt) at room temperature. After two hours the slides where washed for 2 min in a wash buffer containing 2×SSC (Sigma-Aldrich, St. Louis, USA)+0.1% Sarkosyl (RT) (VWR, International Ltd., Poole, United Kingdom) and then for 2 min in 2×SSC (Sigma-Aldrich). The slides were then placed in a beaker with ultra pure $H_2O$ (100° C.) for 2 min and immediately transferred to a beaker containing 100% ethanol (−20° C.). for 20 sec, before they were dried by centrifugation at 91 G in a Multifuge 3 S-R centrifuge (Heraeus, Buckinghamshire, United Kingdom) for 12 min and used within an hour.

Immediately prior the actual array hybridization 60 µl hybridization buffer containing 7.2% Polyethylene glycol 8000 (Sigma-Aldrich), 1.2×SSC (Sigma-Aldrich) and 0.17 µM of the hybridization control probe HYC01 mixture (1:4 mix of tamra labeled HYC01 and unlabeled HYC01) were added to the samples. The samples were denatured at 95° C. for 2 min and then left at 45° C. for 2 min. The glass-slides were placed in a 96-well hybridization chamber (ArrayIt) before the samples were loaded onto the arrays. Two arrays per slide were used for the positive and negative control samples. The hybridization chamber was placed in a humid chamber and hybridized for 16 hours in an Innova 4000 incubator shaker (New Brunswick Scientific, Champaign, USA) at 45° C. and 60 rpm.

After hybridization the arrays were washed for 5 minutes in the wash buffer containing 2×SSC (Sigma-Aldrich) and 0.1% Sarkosyl (VWR, International Ltd.), then for 5 min in 2×SSC (Sigma-Aldrich) and finally for 10 sec in 0.2×SSC (Sigma-Aldrich), before they were dried by centrifugation at 91 G for 12 min in a Multifuge 3 S-R centrifuge (Heraeus). Hybridized arrays were scanned at wavelength 532 nm with a Tecan LS reloaded scanner (Tecan, Männedorf, Austria). Fluorescent intensities and spot morphologies were analyzed using Axon GenePix Pro 6.0.

Data Preprocessing and Analysis

Probe signals were corrected for undesired hybridization variations that are observed from slide to slide. In each experiment, a probe that is already labelled (HYC01) is added to the probe mixture to evaluate the hybridization step. To correct for varying hybridization between slides, all sample signals were divided on the average signal of all replica from this probe. In addition, background signal from each individual probes was removed by subtracting the average signals from a negative control sample included on all slides used in this experiment. Probes emitting a maximum signal of less than 5.5 were removed from the analysis Statistical Analyses and Results Microarray data (Table 4) was analysed by partial least squares discriminant analysis (PLS-DA). PLS-DA is the special case of Partial Least Squares Regression (PLSR) where the response variable is categorical (e.g. patient/control). PLS-DA is based on the same principles as Principal Component Analysis (PCA). PCA uses only X matrix (e.g. probe signals) to find direction of maximum variance in X. PLS-DA makes use of the response variable y (e.g. patient/control) to find combination of weights of variables in X (probe signals) that classify the data with smallest prediction error. In the present experiment correlation between probe signals is usual and so PLS-DA is used to (1) remove the variables (probes) that explain similar characteristics concerning our response, (2) combine them to fewer, new regression variables or (3) to do both of these actions. PLS-DA therefore forms a model between the intensity of all probe signals and the categories (e.g. disease state) by combining the contribution of different probes. For easy comparison these models can be plotted together in a graphical representation, e.g. such as FIG. 1 and FIG. 2. As can be seen from these Figures, in such representations the models of microbiota profiles from samples from infants that developed NEC cluster together (the models, and therefore microbiota profiles of these subjects, can therefore be said to be significantly similar or significantly correlated in accordance with the invention) and the models of microbiota profiles from samples from infants that did not develop NEC cluster together. These microbiota profiles (and corresponding PLS-DA models) can therefore be used as standards to which the results from test samples can be compared in accordance with the methods of the invention.

TABLE 4

| Patient ID | Sample ID | External ID | Age (days) | Age when diagnosed v | Sample collection relative to NEC diagnosis (Days) | Abx treatments 1-3 days prior to sampling | IG0028 Actinobacteria | IG0095 Anaerococcus prevotii | IG0060 Bacteroides | IG0030 Bifidobacterium breve | IG0027 Bifidobacterium longum | IG0163 Clostridium butyricum | IG0058 Clostridium difficile | IG0103 Clostridium sporogenes | IG0178 Enterobacter |
|---|---|---|---|---|---|---|---|---|---|---|---|---|---|---|---|
| 4 | 53 | BI-37-12 | 12 | 27 | −15 | 1 | — | 1.5 | — | 0.3 | 0.1 | 0.3 | 0.5 | — | 79.1 |
| 4 | 54 | BI-37-17 | 17 | 27 | −10 | 1 | — | — | — | 0.3 | 0.8 | 0.4 | 0.2 | — | 131.6 |
| 4 | 55 | BI-37-21 | 21 | 27 | −6 | 1 | 1.0 | — | — | — | 0.6 | 0.4 | — | — | 146.4 |
| 4 | 56 | BI-37-24 | 24 | 27 | −3 | 1 | — | — | — | — | — | 0.3 | — | — | 132.3 |
| 4 | 57 | BI-37-27 | 27 | 27 | 0 | 0 | — | — | — | — | 0.3 | 0.3 | — | — | 143.2 |
| 4 | 64 | BI-86-7 | 7 | 12 | −5 | 1 | — | 4.2 | — | — | — | — | — | — | 43.5 |
| 13 | 65 | BI-86-10 | 10 | 12 | −2 | 0 | 0.7 | 0.6 | — | — | — | — | 0.4 | — | 93.3 |
| 13 | 66 | BI-86-11 | 11 | 12 | −1 | 0 | 0.0 | 0.4 | — | — | — | — | 0.2 | — | 80.9 |
| 13 | 67 | BI-86-12 | 12 | 12 | 0 | 0 | 1.2 | 2.5 | — | 0.6 | — | — | 1.7 | — | 62.4 |
| 16 | 69 | BI-108-6 | 6 | 11 | −5 | 0 | 1.0 | 4.6 | — | 0.6 | — | — | 3.2 | — | — |
| 16 | 70 | BI-108-8 | 8 | 11 | −3 | 0 | 1.5 | 6.5 | — | 0.5 | — | — | 2.4 | — | — |
| 16 | 71 | BI-108-9 | 9 | 11 | −2 | 0 | 1.7 | 5.3 | — | 0.4 | — | — | 3.5 | — | — |
| 16 | 72 | BI-108-10 | 10 | 11 | −1 | 0 | — | 4.1 | — | — | — | — | 4.9 | — | 10.7 |
| 16 | 73 | BI-108-11 | 11 | 11 | 0 | 1 | — | 4.2 | 1.5 | — | — | — | 3.2 | — | 54.0 |
| 5 | 82 | BI-51-17 | 17 | | −10 | 1 | — | 0.7 | 22.4 | — | 2.9 | 0.3 | — | — | 78.9 |
| 5 | 83 | BI-51-21 | 21 | | −6 | 0 | — | — | — | — | — | 0.3 | — | — | 114.0 |
| 5 | 84 | BI-51-24 | 24 | | −3 | 0 | — | 0.0 | — | — | — | 0.4 | — | — | 90.0 |
| 5 | 85 | BI-51-27 | 27 | | 0 | 0 | — | — | — | — | — | — | 0.2 | — | — |
| 6 | 108 | BI-125-17 | 17 | | −9 | 0 | — | 3.6 | — | — | — | — | — | — | — |
| 6 | 109 | BI-125-20 | 20 | | −6 | 0 | — | 5.7 | — | — | — | — | — | — | — |
| 6 | 110 | BI-125-24 | 24 | | −2 | 0 | — | 4.8 | 10.7 | — | 0.6 | — | 0.9 | — | 15.3 |
| 6 | 111 | BI-125-26 | 26 | | 0 | 0 | — | 3.4 | — | — | — | — | 1.3 | — | 0.4 |
| 14 | 92 | BI-94-7 | 7 | | −5 | 0 | — | 5.9 | — | — | 0.0 | — | — | — | 0.3 |
| 14 | 93 | BI-94-10 | 10 | | −2 | 0 | — | 7.5 | — | — | — | — | — | — | — |
| 14 | 94 | BI-94-11 | 11 | | −1 | 0 | — | 15.4 | — | — | — | — | — | — | — |
| 14 | 95 | BI-94-12 | 12 | | 0 | 0 | 0.4 | 12.6 | — | 0.1 | — | — | 0.8 | — | 57.7 |
| 15 | 117 | BI-25-7 | 7 | | −5 | 0 | — | 2.6 | — | — | — | — | 18.3 | — | 80.2 |
| 15 | 118 | BI-25-10 | 10 | | −2 | 0 | — | 4.5 | — | — | — | — | 22.1 | — | 113.5 |
| 15 | 119 | BI-25-11 | 11 | | −1 | 0 | — | 3.7 | — | — | — | — | 23.4 | — | 99.7 |
| 15 | 120 | BI-25-12 | 12 | | 0 | 0 | 0.7 | 3.7 | — | — | — | — | 16.6 | — | 16.1 |
| 17 | 96 | BI-116-6 | 6 | | −5 | 0 | 1.0 | 4.2 | — | 0.4 | — | — | — | — | — |
| 17 | 97 | BI-116-8 | 8 | | −3 | 0 | 2.0 | 2.9 | — | 0.5 | — | — | — | — | — |
| 17 | 98 | BI-116-9 | 9 | | −2 | 0 | — | 2.3 | — | — | — | — | — | — | — |
| 17 | 99 | BI-116-10 | 10 | | −1 | 0 | 1.7 | 2.8 | — | 0.6 | — | — | 1.2 | — | — |
| 17 | 100 | BI-116-11 | 11 | | 0 | 0 | 1.6 | 1.8 | — | 0.1 | — | — | 0.7 | — | — |
| 18 | 121 | BI-118-6 | 6 | | −5 | 0 | 1.8 | 4.3 | — | 0.3 | — | — | 2.2 | — | 0.1 |
| 18 | 122 | BI-118-8 | 8 | | −3 | 0 | 1.1 | 4.5 | — | — | — | — | 7.6 | — | 0.8 |
| 18 | 123 | BI-118-9 | 9 | | −2 | 0 | 0.2 | 3.6 | — | — | — | — | 10.9 | — | 0.3 |
| 18 | 124 | BI-118-10 | 10 | | −1 | 0 | — | 2.4 | — | — | — | — | 7.5 | — | 0.2 |
| 18 | 125 | BI-118-11 | 11 | | 0 | 0 | 1.5 | 0.7 | — | 0.1 | 0.0 | — | — | — | — |
| | | | | | | | IG0023 Firmicutes (Clostridia, | IG0012 (Lactoba- | IG0056 Gamma- | | | | | | IG0195 |

TABLE 4-continued

| Patient ID | Sample ID | IG0168 Enterococcus | IG0107 Finegoldia magna | Bacillales, Enterococcus, Firmicutes | cillales, Clostridium perf.. | proteobacteria subgroup | IG0042 Gemella | IG0008 Haemophilus | IG0181 Klebsiella | IG0053 Lactobacilli | IG0021 Listeria | IG0044 Megashpaera | IG0005 Proteobacteria | IG0039 Pseudomonas | Raoultella-Kluyvera |
|---|---|---|---|---|---|---|---|---|---|---|---|---|---|---|---|
| 4 | 53 | 6.0 | 1.4 | 41.4 | 32.4 | 11.3 | — | — | 1.7 | 13.1 | — | 1.4 | 127.4 | 80.0 | 5.2 |
| 4 | 54 | — | 0.8 | 4.7 | 0.5 | 11.8 | — | — | 2.0 | 11.3 | — | 0.3 | 162.4 | 33.1 | 8.0 |
| 4 | 55 | — | 0.7 | 4.4 | 0.9 | 15.6 | 0.0 | — | 2.4 | 14.9 | — | 0.1 | 147.1 | 29.7 | 13.8 |
| 4 | 56 | — | 0.0 | 4.7 | 4.6 | 16.3 | — | 0.0 | 0.6 | 10.2 | — | — | 162.0 | 2.4 | 6.4 |
| 4 | 57 | — | 1.0 | 1.6 | 2.1 | 15.0 | — | — | 1.2 | 9.1 | — | — | 135.2 | 2.4 | 5.9 |
| 13 | 64 | 7.5 | 0.0 | 93.4 | 42.2 | 42.3 | — | 0.0 | 7.6 | 2.2 | — | 2.1 | 59.0 | 3.7 | 2.4 |
| 13 | 65 | 17.1 | 0.6 | 29.7 | 33.0 | 96.3 | — | — | 24.0 | 2.7 | — | 0.3 | 155.7 | 4.2 | 6.4 |
| 13 | 66 | 19.1 | 0.3 | 20.8 | 31.0 | 104.4 | — | — | 24.9 | 3.9 | — | 0.1 | 136.0 | 3.2 | 6.4 |
| 13 | 67 | 61.8 | 1.1 | 67.0 | 94.8 | 65.4 | — | 0.3 | 13.0 | 2.2 | — | 0.5 | 96.3 | 3.7 | 6.3 |
| 16 | 69 | 84.1 | 1.0 | 118.1 | 143.4 | 0.9 | — | 0.0 | — | 2.4 | — | 0.8 | — | 4.9 | 3.8 |
| 16 | 70 | 87.7 | 1.4 | 128.7 | 153.7 | 0.7 | — | — | — | 1.8 | — | 1.5 | — | 6.3 | — |
| 16 | 71 | 83.6 | 1.0 | 152.5 | 176.6 | 0.9 | 0.1 | — | — | 5.3 | — | 1.4 | — | 6.4 | — |
| 16 | 72 | 94.3 | 0.3 | 142.3 | 158.5 | 0.1 | — | — | — | 5.7 | — | 1.1 | — | 7.1 | 1.3 |
| 16 | 73 | 71.0 | — | 112.3 | 136.4 | 4.6 | — | 5.4 | 0.7 | 6.7 | — | 1.2 | 19.5 | 6.4 | 4.4 |
| 5 | 82 | 11.1 | — | 31.5 | 97.1 | 6.8 | — | — | — | 11.4 | — | — | 103.6 | 3.7 | 5.6 |
| 5 | 83 | — | — | 1.3 | 3.2 | 8.3 | — | — | — | 9.4 | — | 0.0 | 119.0 | 2.8 | 9.8 |
| 5 | 84 | 5.5 | — | 14.7 | 29.8 | 12.4 | — | — | — | 11.6 | — | 0.3 | 158.4 | 3.3 | 7.3 |
| 5 | 85 | 6.8 | 0.1 | 10.6 | 20.9 | 14.4 | — | — | 0.0 | 17.6 | — | — | 168.3 | 4.9 | — |
| 6 | 108 | — | — | 41.6 | 18.9 | — | — | 0.6 | — | — | — | 1.5 | — | 2.6 | — |
| 6 | 109 | 21.5 | — | 92.9 | 82.9 | — | — | 0.2 | — | 0.9 | — | 2.3 | — | 4.5 | — |
| 6 | 110 | 52.2 | — | 97.0 | 97.1 | — | — | — | — | 6.6 | — | 0.6 | 1.9 | 4.9 | — |
| 6 | 111 | 60.8 | — | 97.8 | 150.7 | 0.7 | — | — | — | 8.9 | — | 0.4 | 25.2 | 4.9 | 0.7 |
| 14 | 92 | 4.2 | — | 105.6 | 76.6 | — | — | — | — | 8.3 | — | 3.1 | 1.4 | 4.8 | — |
| 14 | 93 | — | — | 60.8 | 191.5 | — | — | — | — | 8.3 | — | 0.6 | 0.4 | 8.9 | — |
| 14 | 94 | — | — | 114.9 | 193.7 | — | 0.0 | — | — | 14.5 | — | 3.9 | 0.1 | 20.3 | — |
| 14 | 95 | — | 0.3 | 25.4 | 158.9 | 0.7 | — | 150.9 | 0.3 | 26.0 | — | 1.8 | 46.3 | 16.3 | — |
| 15 | 117 | 44.3 | 2.5 | 79.7 | 131.1 | 4.2 | — | 128.2 | 0.4 | 16.3 | — | 5.5 | 38.7 | 5.2 | — |
| 15 | 118 | 54.2 | 5.3 | 92.2 | 143.3 | 2.7 | — | 83.6 | — | 4.0 | — | 9.1 | 25.3 | 7.3 | — |
| 15 | 119 | 49.0 | 3.0 | 73.3 | 122.0 | 1.7 | — | 114.9 | — | 8.3 | — | 13.4 | 22.0 | 7.5 | — |
| 15 | 120 | 69.4 | 3.8 | 82.0 | 142.5 | 2.6 | — | — | — | 6.2 | — | 13.7 | 95.6 | 6.6 | — |
| 17 | 96 | — | 0.8 | 74.4 | 23.4 | 5.7 | — | — | — | 5.8 | — | 4.4 | 134.6 | 5.6 | — |
| 17 | 97 | — | 1.1 | 57.5 | 13.1 | 7.8 | — | 0.2 | 0.3 | 4.7 | — | 1.6 | 144.4 | 3.7 | — |
| 17 | 98 | — | 0.7 | 50.0 | 32.4 | 7.6 | — | — | 0.4 | 3.7 | — | 0.9 | 83.9 | 2.6 | — |
| 17 | 99 | — | — | 47.3 | 161.8 | 1.7 | — | — | 0.4 | 3.3 | — | 0.3 | 58.7 | 1.7 | — |
| 17 | 100 | — | 1.5 | 42.4 | 109.1 | 5.6 | — | 92.2 | — | — | — | 0.9 | — | 1.5 | — |
| 18 | 121 | 3.3 | 0.2 | 98.1 | 53.1 | — | — | 0.1 | — | 6.2 | — | 4.2 | 0.1 | 3.7 | — |
| 18 | 122 | 15.9 | 0.5 | 113.5 | 90.8 | 0.2 | — | 35.1 | — | 3.9 | — | 2.5 | 8.8 | 4.3 | — |
| 18 | 123 | 2.3 | 0.1 | 63.8 | 78.7 | 0.3 | — | 92.4 | — | 3.5 | — | 3.7 | 22.5 | 3.7 | — |
| 18 | 124 | 3.3 | 0.0 | 55.2 | 79.9 | 1.6 | 0.1 | 92.3 | — | 1.1 | — | 3.3 | 11.5 | 3.5 | — |
| 18 | 125 | 6.5 | 0.5 | 19.8 | 41.6 | 0.7 | 0.1 | 41.6 | — | — | — | 1.4 | 11.5 | 1.5 | 0.0 |

| Patient ID | Sample ID | IG0011 Salmonella | IG0204 Serratia | IG0133 Shigella and Ecoli | IG0024 Staphylococcus | IG0063 Staphylococcus epidermidis | IG0081 Streptococcus agalacticae | IG0197 Streptococcus genomsp 7 | IG0079 Streptococcus mitis | IG0022 Streptococcus pneumonia | IG0020 Streptococcus sanguinis | IG0051 Veillonella |
|---|---|---|---|---|---|---|---|---|---|---|---|---|
| 4 | 53 | 24.2 | 6.7 | — | 20.3 | 58.8 | 4.3 | — | 0.6 | 2.6 | — | 2.3 |
| 4 | 54 | 50.0 | 8.8 | — | 4.4 | 2.7 | — | 0.3 | 0.8 | 0.8 | — | 1.9 |
| 4 | 55 | 38.0 | 14.6 | 12.2 | — | 1.2 | 0.1 | 0.0 | 0.3 | 0.0 | — | 1.4 |

TABLE 4-continued

| | | | | | | | | | | | | |
|---|---|---|---|---|---|---|---|---|---|---|---|---|
| 4 | 56 | 35.8 | 0.6 | — | — | — | 0.1 | — | — | — | — | 1.3 |
| 4 | 57 | 28.1 | 0.5 | — | — | — | 7.2 | — | — | — | — | 1.6 |
| 13 | 64 | — | — | — | 3.4 | 112.2 | — | — | — | — | — | 0.3 |
| 13 | 65 | — | — | 20.3 | 44.9 | 11.4 | 2.1 | — | — | — | — | 1.8 |
| 13 | 66 | — | — | 32.4 | 5.4 | 4.5 | 5.9 | — | — | — | — | 1.7 |
| 13 | 67 | — | — | — | — | — | 7.6 | — | — | 31.1 | — | 1.6 |
| 16 | 69 | — | — | — | 13.6 | 41.8 | 9.1 | — | — | — | — | 0.7 |
| 16 | 70 | — | — | — | 28.8 | 86.2 | 1.8 | — | — | — | — | 0.7 |
| 16 | 71 | — | — | — | 45.3 | 115.8 | 1.3 | — | — | — | — | 0.8 |
| 16 | 72 | — | — | — | 37.6 | 114.3 | — | — | — | — | — | 0.1 |
| 16 | 73 | — | — | 1.4 | 18.7 | 60.8 | 0.5 | 0.1 | 1.2 | — | 0.2 | — |
| 5 | 82 | — | — | — | 17.5 | 33.3 | — | 6.8 | — | 45.5 | 2.2 | 0.9 |
| 5 | 83 | — | — | — | — | — | 4.7 | — | — | 121.0 | — | 1.3 |
| 5 | 84 | — | — | 4.4 | 0.1 | 3.9 | 7.1 | — | — | 0.2 | — | 1.2 |
| 5 | 85 | — | — | — | 2.4 | — | 2.1 | — | — | 3.4 | — | 2.2 |
| 6 | 108 | — | — | — | 21.1 | 92.4 | 3.6 | — | — | — | 0.6 | — |
| 6 | 109 | — | — | — | 41.7 | 136.3 | 15.5 | 1.6 | 0.1 | — | 0.1 | — |
| 6 | 110 | — | 0.2 | — | 21.9 | 65.8 | 5.8 | 0.1 | 0.1 | 41.5 | 0.0 | — |
| 6 | 111 | — | 0.3 | 7.2 | 17.7 | 45.0 | 11.1 | — | — | 30.3 | — | — |
| 14 | 92 | — | — | — | 49.9 | 156.6 | 0.4 | — | — | — | — | 2.2 |
| 14 | 93 | — | — | — | 31.6 | 61.4 | 0.1 | 39.9 | 76.0 | — | 18.0 | 0.1 |
| 14 | 94 | — | — | — | 56.3 | 108.8 | 0.4 | 88.3 | 112.6 | — | 22.4 | 2.9 |
| 14 | 95 | — | — | — | 16.4 | 24.4 | 0.3 | 82.2 | 104.4 | — | 25.2 | 1.5 |
| 15 | 117 | — | — | 0.6 | 6.5 | 5.2 | 0.9 | — | — | 24.9 | — | 2.0 |
| 15 | 118 | — | — | — | 7.4 | 9.5 | 6.5 | — | — | 36.3 | — | 4.8 |
| 15 | 119 | — | — | — | 8.2 | 9.1 | 6.3 | — | — | 33.2 | — | 9.6 |
| 15 | 120 | — | — | — | 3.9 | 16.7 | 3.6 | — | — | 22.6 | — | 1.8 |
| 17 | 96 | — | — | — | 39.5 | 112.7 | 3.2 | — | — | — | — | 1.4 |
| 17 | 97 | — | — | — | 39.7 | 94.9 | 1.3 | — | — | — | — | 1.1 |
| 17 | 98 | — | — | — | 34.4 | 70.7 | 10.0 | — | — | — | — | — |
| 17 | 99 | — | — | — | 35.9 | 76.9 | 8.6 | — | — | — | — | 1.5 |
| 17 | 100 | — | — | — | 28.0 | 38.5 | 3.9 | — | — | — | — | 0.7 |
| 18 | 121 | — | — | — | 52.9 | 101.7 | 2.7 | — | — | — | — | 1.0 |
| 18 | 122 | — | — | — | 66.8 | 117.3 | 1.1 | 0.1 | 0.1 | — | — | 0.8 |
| 18 | 123 | — | — | — | 32.5 | 70.5 | — | 0.1 | — | 0.2 | — | 0.7 |
| 18 | 124 | — | — | — | 22.8 | 35.0 | — | 0.1 | — | — | — | 1.3 |
| 18 | 125 | — | — | — | 4.7 | 12.9 | — | 0.2 | 0.3 | 3.2 | 0.0 | — |

The invention claimed is:

1. A method for identifying a neonatal subject at risk for NEC, said method comprising
   (a) profiling the microbiota in a sample from the GI tract of said subject prior to a conclusive diagnosis of NEC and/or prior to full onset of NEC, wherein said microbiota profiling comprises a step of determining the amounts of a plurality of nucleotide sequences each of which is characteristic of a different type of microorganism present in said sample,
   (b1) comparing said profile to a standard microbiota profile obtained from corresponding samples from neonatal subjects with NEC or subjects which later developed NEC and determining the degree of correlation between said profile and the standard profile(s), and/or
   (b2) comparing said profile to a standard microbiota profile obtained from corresponding samples from neonatal subjects which did not develop NEC and determining the degree of correlation between said profile and the standard profile, and
   (c) identifying the subject as being at risk of NEC if significant correlation is observed in (b1) and/or significant correlation is not seen in (b2).

2. The method of claim 1 wherein the subject is identified as being at risk of NEC if a more significant correlation is observed in (b1) than the correlation seen in (b2).

3. The method of claim 1 wherein the microbiota profile is obtained prior to the onset of detectable symptoms of NEC.

4. The method of claim 1 wherein microbiota profiling step (a) comprises
   (i) contacting the sample with an oligonucleotide probe set comprising a plurality of oligonucleotide probes that are capable of hybridising to nucleotide sequences present in the nucleic acids of microorganisms that are characteristic of particular microorganisms or groups of microorganisms;
   (ii) subjecting the sample and the probe set to conditions which allow hybridisation of the probes to their target nucleotide sequences within nucleic acid molecules in said sample; and
   (iii) for each oligonucleotide in said probe set, determining the amount of its target nucleotide sequence that is present in said sample, and
   (iv) determining the profile of the microbiota in the sample from the relative amounts of said target sequence.

5. The method of claim 4 wherein each oligonucleotide has a label attached thereto, and step (iii) comprises determining, for each labelled oligonucleotide, the amount of said label bound to said sample by determining the strength of the signal from the label emanating from the sample.

6. The method of claim 4 wherein step (iii) comprises
   (iii)(a) selectively labelling the oligonucleotide probes of the probe set when hybridised to their target nucleotide sequence; and
   (iii)(b) determining the amount of each labelled oligonucleotide probe produced in step (iii)(a).

7. The method of claim 6 wherein selective labelling occurs by chain extension of the oligonucleotide probe with a labelled nucleotide, preferably a labelled dideoxynucleotide.

8. The method of claim 7 wherein said labelled nucleotide is a labelled ddCTP, preferably ddCTP labelled with biotin.

9. The method of claim 6 wherein step (iii)(b) comprises hybridisation of the oligonucleotides from labelling step (iii)(a) to nucleotide sequences complementary to the oligonucleotide probes.

10. The method of claim 9 wherein one or more of said nucleotide sequences complementary to the oligonucleotide probes is immobilised on one or more solid supports, preferably selected from particles, sheets, gels, filters, membranes, fibres, capillaries, chips, microtitre strips, slides, tubes, plates or wells.

11. The method of claim 10 wherein said solid support is a magnetic particle, preferably a magnetic bead.

12. The method of claim 10 wherein said solid support is labelled with a dye or a plurality of dyes, preferably a luminescent dye.

13. The method of claim 4 wherein step (iii) comprises
    (iii)(a) performing a primer-dependent nucleic acid amplification reaction; and
    (iii)(b) for each oligonucleotide in the probe set determining the amount of amplification product produced therefrom in said primer-dependent nucleic acid amplification reaction.

14. The method of claim 13 wherein said primer-dependent nucleic acid amplification reaction is PCR.

15. The method of claim 13 wherein said primer-dependent nucleic acid amplification reaction is a plurality of primer dependent nucleic acid amplification reactions being run in parallel, with each parallel amplification reaction involving a single oligonucleotide probe, or one or more multiplex primer dependent nucleic acid amplification reactions being run with two or more oligonucleotide probes being used in the same multiplex amplification reaction.

16. The method of claim 4 wherein said oligonucleotide probe set comprises
    (a) an oligonucleotide comprising a nucleotide sequence selected from CACATGAGCGTCAGTACATTCC (SEQ ID NO 1), the sequence complementary thereto (GGAATGTACTGACGCTCATGTG; SEQ ID NO 36) or a sequence capable of hybridising to either sequence under conditions of high stringency;
    (b) an oligonucleotide comprising a nucleotide sequence selected from TGTTGTGGTTAATAACCGCAG-CAATTGA (SEQ ID NO 2), the sequence complementary thereto (TCAATTGCTGCGGTTATTAACCA-CAACA; SEQ ID NO 37) or a sequence capable of hybridising to either sequence under conditions of high stringency;
    (c) an oligonucleotide comprising a nucleotide sequence selected from GGACAACGCTTGCCAC (SEQ ID NO 3), the sequence complementary thereto (GTG-GCAAGCGTTGTCC; SEQ ID NO 38) or a sequence capable of hybridising to either sequence under conditions of high stringency;
    (d) an oligonucleotide comprising a nucleotide sequence selected from ACCGCTACACAGGAAATT (SEQ ID NO 4), the sequence complementary thereto (AATTTC-CTGTGTAGCGGT; SEQ ID NO 39) or a sequence capable of hybridising to either sequence under conditions of high stringency;
    (e) an oligonucleotide comprising a nucleotide sequence selected from GGAATTCCACTTTCCTCTC-CGATACT (SEQ ID NO 5), the sequence complementary thereto (AGTATCGGAGAGGAAAGTGGAAT-TCC; SEQ ID NO 40) or a sequence capable of hybridising to either sequence under conditions of high stringency;
    (f) an oligonucleotide comprising a nucleotide sequence selected from GCACCTGTCTCACAGTT (SEQ ID NO 6), the sequence complementary thereto (AACTGT-GAGACAGGTGC; SEQ ID NO 41) or a sequence capable of hybridising to either sequence under conditions of high stringency (
    g) an oligonucleotide comprising a nucleotide sequence selected from GTTTCCAATGACCCTCC (SEQ ID NO 7), the sequence complementary thereto (GGAGGGT-CATTGGAAAC; SEQ ID NO 42) or a sequence capable of hybridising to either sequence under conditions of high stringency or an oligonucleotide comprising a nucleotide sequence selected from CGTCAGGG-GACGTT (SEQ ID NO 8), the sequence complementary thereto (AACGTCCCCTGACG; SEQ ID NO 43) or a sequence capable of hybridising to either sequence under conditions of high stringency;
    (h) an oligonucleotide comprising a nucleotide sequence selected from CCCCGCTGAAAGTG (SEQ ID NO 9), the sequence complementary thereto (CACTTTCAGCGGGG; SEQ ID NO 44) or a sequence capable of hybridising to either sequence under conditions of high stringency;
    (i) an oligonucleotide comprising a nucleotide sequence selected from CACTCCTCAAGGGAACAA (SEQ ID NO 10), the sequence complementary thereto (TTGT-TCCCTTGAGGAGTG; SEQ ID NO 45) or a sequence capable of hybridising to either sequence under conditions of high stringency; and
    (j) an oligonucleotide comprising a nucleotide sequence selected from AGCGTATTAAGCTCACCA (SEQ ID NO 11), the sequence complementary thereto (TGGT-GAGCTTAATACGCT; SEQ ID NO 46) or a sequence capable of hybridising to either sequence under conditions of high stringency.

17. A method for identifying a neonatal subject at risk for NEC, said method comprising
    (a) profiling the microbiota in a sample from the GI tract of said subject prior to a conclusive diagnosis of NEC and/or prior to full onset of NEC wherein said microbiota profiling comprises
        (i) contacting the sample with a set of interactive proteins that can bind selectively to peptide sequences characteristic of specific microorganisms;
        (ii) subjecting the sample and the set of interactive proteins to conditions which allow binding of the set of interactive proteins to their target peptide sequences within said sample;
        (iii) for each interactive protein in said set, determining the amount of its target peptide sequence that is present in said sample; and
        (iv) determining the profile of the microbiota in the sample from the relative amounts of said target sequence,
    (b1) comparing said profile to a standard microbiota profile obtained from corresponding samples from neonatal subjects with NEC or subjects which later developed NEC and determining the degree of correlation between said profile and the standard profile(s), and/or
    (b2) comparing said profile to a standard microbiota profile obtained from corresponding samples from neonatal subjects which did not develop NEC and determining the degree of correlation between said profile and the standard profile, and
    (c) identifying the subject as being at risk of NEC if significant correlation is observed in (b1) and/or significant correlation is not seen in (b2).

18. The method of claim 1 wherein said sample from the GI tract is selected from (a) luminal contents of the GI tract, preferably stomach contents, intestinal contents, mucus and faeces/stool, or combinations thereof, (b) parts of the mucosa, the submucosa, the muscularis externa, the adventitia and/or the serosa of a GI tract tissue/organ, or (c) nucleic acid prepared from (a) or (b), preferably by reverse transcription and/or nucleic acid amplification.

19. The method of claim 17 wherein the subject is identified as being at risk of NEC if a more significant correlation is observed in (b1) than the correlation seen in (b2).

20. The method of claim 17 wherein the microbiota profile is obtained prior to the onset of detectable symptoms of NEC.

21. The method of claim 17 wherein said sample from the GI tract is selected from (a) luminal contents of the GI tract, preferably stomach contents, intestinal contents, mucus and faeces/stool, or combinations thereof, or (b) parts of the mucosa, the submucosa, the muscularis externa, the adventitia and/or the serosa of a GI tract tissue/organ.

* * * * *